United States Patent
Taguchi et al.

(10) Patent No.: US 7,456,002 B2
(45) Date of Patent: Nov. 25, 2008

(54) MUTANT POLY(3-HYDROXYALKANOIC ACID) SYNTHASES

(75) Inventors: Seiichi Taguchi, Saitama (JP); Kazuma Takase, Saitama (JP); Yoshiharu Doi, Saitama (JP)

(73) Assignee: Riken, Wako-shi (JP)

( * ) Notice: Subject to any disclaimer, the term of this patent is extended or adjusted under 35 U.S.C. 154(b) by 351 days.

(21) Appl. No.: 10/515,645

(22) PCT Filed: May 9, 2003

(86) PCT No.: PCT/JP03/05839

§ 371 (c)(1),
(2), (4) Date: Nov. 24, 2004

(87) PCT Pub. No.: WO03/100055

PCT Pub. Date: Dec. 4, 2003

(65) Prior Publication Data

US 2007/0054386 A1    Mar. 8, 2007

(30) Foreign Application Priority Data

May 28, 2002   (JP) ............................ 2002-154374

(51) Int. Cl.
  C12N 9/18    (2006.01)
  C12N 9/00    (2006.01)
  C12P 7/62    (2006.01)
  C12P 21/06   (2006.01)
  C08G 63/00   (2006.01)
  C07H 21/04   (2006.01)

(52) U.S. Cl. .................. 435/193; 435/183; 435/135; 435/69.1; 528/274; 536/23.2

(58) Field of Classification Search .................. 435/197, 435/135, 69.1; 523/124; 528/274; 536/23.2
See application file for complete search history.

(56) References Cited

FOREIGN PATENT DOCUMENTS

EP    1 120 461 A1    8/2001

OTHER PUBLICATIONS

Hiromi Matsusaki et al., Journal of Bacteriology, Dec. 1998, vol. 180, No. 24, pp. 6459 to 6467.
A.A. Amara et al., Appl. Microbiol. Biotechnol., 2002, vol. 59, pp. 477 to 482.
Yong Jia et al., Biochemistry 2001, vol. 40, pp. 1011 to 1019.
Bernd H.A. Rehm et al., Biochimica et Biophysica Acta 2002, vol. 1594, pp. 178 to 190.
Taguchi et al., Polymer Preprints of the Society of Polymer Science, Japan, vol. 51, No. 1, p. 950, (May 29-31, 2002) (and English Translation).

*Primary Examiner*—Rebecca E. Prouty
*Assistant Examiner*—Iqbal H Chowdhury
(74) *Attorney, Agent, or Firm*—Birch, Stewart, Kolasch & Birch, LLP

(57) ABSTRACT

Biodegradable polyester with desired physical properties.

A mutant poly(3-hydroxyalkanoic acid) synthase comprising an amino acid sequence of (a) or (b) below.

(a) A mutant amino acid sequence derived from SEQ ID No. 1, wherein at least one amino acid selected from the group consisting of glutamic acid at position 130, serine at position 325, serine at position 477 and glutamine at position 481 is substituted by another amino acid.

(b) A mutant amino acid sequence derived from SEQ ID No. 1 wherein at least one amino acid selected from the group consisting of glutamic acid at position 130, serine at position 325, serine at position 477 and glutamine at position 481 is substituted by another amino acid, wherein at least one amino acid other than the amino acids at positions 130, 325, 477 and 481 is deleted, substituted and/or added, wherein the mutant amino acid sequence has the activity to biosynthesize biodegradable polyester.

18 Claims, 13 Drawing Sheets

MUTANT POLY(3-HYDROXYALKANOIC ACID) SYNTHASES

TECHNICAL FIELD

The present invention relates to a mutant poly(3-hydroxyalkanoic acid) synthase that can produce biodegradable polyester with desired physical properties.

BACKGROUND ART

As part of an attempt to establish a sustainable society, the production of eco-friendly biodegradable plastics is noted. Because poly(3-hydroxyalkanoic acid) (PHA) produced by microorganisms such as *Ralstonia eutropha* has both thermoplasticity and biodegradability, its applications as biodegradable plastics have been studied, with some already put in practical use.

Establishing a less costly production system and breeding microorganisms that can produce biodegradable plastics so as to show desired properties are important for wider use of biodegradable plastics. To achieve this, new types of biodegradable polyester synthases have been explored, enzyme production has been enhanced using genetic engineering methods, and metabolic engineering approaches have been applied to alter intracellular biosynthetic pathways.

For copolymer biodegradable plastics, for example, it is possible to control their physical properties by varying monomer ratios. However, no efficient method for modifying the monomer ratios of copolymers has been established, so biodegradable plastics with desired physical properties have not yet been obtained.

DISCLOSURE OF THE INVENTION

It is an object of the present invention to provide a novel mutant poly(3-hydroxyalkanoic acid) synthase that can produce biodegradable polyester with desired physical properties.

As a result of intensive studies to solve above problems, the inventors have succeeded in modifying an enzyme involved in the biosynthesis of poly(3-hydroxyalkanoic acid) into one with desired properties by evolutionary technologies, and completed the invention.

The present invention includes the following:

(1) A mutant poly(3-hydroxyalkanoic acid) synthase comprising an amino acid sequence of (a) or (b) below.

(a) An amino acid sequence derived from SEQ ID No. 1 wherein at least one amino acid selected from the group consisting of glutamic acid at position 130, serine at position 325, serine at position 477 and glutamine at position 481 is substituted by another amino acid;

(b) An amino acid sequence derived from SEQ ID No. 1 wherein at least one amino acid selected from the group consisting of glutamic acid at position 130, serine at position 325, serine at position 477 and glutamine at position 481 is substituted by another amino acid, wherein at least one amino acid other than the amino acids at positions 130, 325, 477 and 481 is deleted, substituted and/or added, wherein the amino acid sequence has the activity to biosynthesize biodegradable polyester.

(2) The mutant poly(3-hydroxyalkanoic acid) synthase described in (1), characterized in that the aforementioned serine at position 325 is substituted by cysteine or threonine.

(3) The mutant poly(3-hydroxyalkanoic acid) synthase described in (1), characterized in that the aforementioned glutamine at position 481 is substituted by glycine, lysine, leucine, methionine, arginine, serine or threonine.

(4) The mutant poly(3-hydroxyalkanoic acid) synthase described in (1), characterized in that the aforementioned glutamine at position 481 is substituted by lysine, arginine or methionine.

(5) The mutant poly(3-hydroxyalkanoic acid) synthase described in (1), characterized in that the aforementioned glutamic acid at position 130 is substituted by aspartic acid.

(6) The mutant poly(3-hydroxyalkanoic acid) synthase described in (1), characterized in that the aforementioned serine at position 477 is substituted by arginine.

(7) A mutant poly(3-hydroxyalkanoic acid) synthase comprising a mutant amino acid sequence derived from SEQ ID No. 1, characterized in that the mutant amino acid sequence has a mutation selected from the group consisting of a mutation consisting of substitutions from arginine to histidine at position 27 and from serine to arginine at position 477, a mutation consisting of substitutions from glutamic acid to aspartic acid at position 130 and from leucine to phenylalanine at position 327, a mutation consisting of substitutions from glutamine to arginine at position 12, from methionine to leucine at position 362 and from serine to glycine at position 497, a mutation consisting of substitutions from alanine to valine at position 304 and from methionine to leucine at position 369, a mutation consisting of substitutions from aspartic acid to asparagine at position 30 and from asparagine to tyrosine at position 274, a mutation consisting of a substitution from serine to arginine at position 477, and a mutation consisting of a substitution from glutamic acid to aspartic acid at position 130.

(8) A biodegradable polyester produced by the mutant biodegradable polyester synthase described in any one of (1)-(7) above.

(9) A mutant poly(3-hydroxyalkanoic acid) synthase gene encoding the mutant biodegradable polyester synthase described in any one of (1)-(7) above.

The present invention is described in more detail below.

The mutant biodegradable polyester synthase of the invention comprises a mutant amino acid sequence of SEQ ID No. 1, wherein at least one amino acid selected from the group consisting of glutamic acid at position 130, serine at position 325, serine at position 477 and glutamine at position 481 is substituted by another amino acid. The amino acid sequence of SEQ ID No. 1 represents the amino acid sequence of wild-type poly(3-hydroxyalkanoic acid) synthase derived from *Pseudomonas sp.* strain 61-3.

Other amino acids substituting glutamic acid at position 130 may be any amino acid other than glutamic acid, and include but are not limited to, for example, alanine, leucine, isoleucine, valine, serine, proline, tyrosine, phenylalanine, tryptophan, methionine, cysteine, aspartic acid, lysine, arginine, histidine, asparagine, glutamine, threonine and glycine. Particularly, another amino acid substituting glutamic acid at position 130 is preferably aspartic acid.

Other amino acids substituting serine at position 325 may be any amino acid other than serine, and include but are not limited to, for example, alanine, leucine, isoleucine, valine, proline, tyrosine, phenylalanine, tryptophan, methionine, cysteine, aspartic acid, glutamic acid, lysine, arginine, histidine, asparagine, glutamine, threonine and glycine. Particularly, another amino acid substituting serine at position 325 is preferably cysteine or threonine.

Other amino acids substituting serine at position 477 may be any amino acid other than serine, and include but are not limited to, for example, alanine, leucine, isoleucine, valine, proline, tyrosine, phenylalanine, tryptophan, methionine, cysteine, aspartic acid, glutamic acid, lysine, arginine, histidine, asparagine, glutamine, threonine and glycine. Particularly, another amino acid substituting serine at position 477 is preferably arginine.

Other amino acids substituting glutamine at position 481 may be any amino acid other than glutamine, and include but are not limited to, for example, alanine, leucine, isoleucine, valine, proline, tyrosine, phenylalanine, tryptophan, methionine, cysteine, aspartic acid, glutamic acid, lysine, arginine, histidine, asparagine, serine, threonine and glycine. Particularly, another amino acid substituting glutamine at position 481 is preferably glycine, lysine, leucine, methionine, arginine, serine or threonine, and more preferably lysine, arginine or methionine.

"Poly(3-hydroxyalkanoic acid) synthase" is a key enzyme essential for polyester synthesis and catalyzes the polymerization of (R)-3-hydroxyacyl-CoA monomers. Poly(3-hydroxyalkanoic acid) is an ester polymer composed of 3-hydroxyalkanoic acid molecules that are bound by ester bonds, and is biosynthesized by organisms and decomposed by microorganisms in soil and water.

The mutant poly(3-hydroxyalkanoic acid) synthase according to the invention has a mutant amino acid sequence of SEQ ID No. 1 that has a mutation selected from the group consisting of a mutation consisting of substitutions from arginine to histidine at position 27 and from serine to arginine at position 477, a mutation consisting of substitutions from glutamic acid to aspartic acid at position 130 and from leucine to phenylalanine at position 327, a mutation consisting of substitutions from glutamine to arginine at position 12, from methionine to leucine at position 362 and from serine to glycine at position 497, a mutation consisting of substitutions from alanine to valine at position 304 and from methionine to leucine at position 369, a mutation consisting of substitutions from aspartic acid to asparagine at position 30 and from asparagine to tyrosine at position 274, a mutation consisting of a substitution from serine to arginine at position 477, and a mutation consisting of a substitution from glutamic acid to aspartic acid at position 130.

Generally, the biosynthetic pathway of poly(3-hydroxyalkanoic acid) in bacteria consists of two systems; a system to supply monomer units constituting poly(3-hydroxyalkanoic acid) (monomer supply system) and a system to polymerize monomer units (monomer polymerization system), as shown in FIG. 1. For example, as shown in FIGS. 2 and 3, the bacterial biosynthesis of poly(3-hydroxyalkanoic acid) is conducted through the polymerization of monomer units (FIG. 2: (R)-3-hydroxy valeryl-CoA, (R)-3-hydroxybutyryl-CoA; FIG. 3: (R)-3-hydroxyacyl-CoA) by poly(3-hydroxybutanoate) synthase and poly(3-hydroxyalkanoic acid) synthase, which biosynthesized through the acetyl-CoA dimerization system consisting, for example, of 3-keto thiolase (PhbA, BktB) and acetoacetyl-CoA reductase (PhbB), the fatty acid decomposition pathway consisting, for example, of enoyl-CoA hydratase (PhaJ) and 3-ketoacyl-ACP reductase (FabG), and the fatty acid biosynthetic pathway consisting, for example, of (R)-3-hydroxyacyl-ACP-CoA transacylase (PhaG), 3-ketoacyl-ACP synthase III (FabH) and malonyl-CoA-ACP transacylase (FabD). Poly(3-hydroxybutanoate) is a homopolymer of 3-hydroxybutanoic acid, and poly(3-hydroxyalkanoic acid) indicates a wide range of 3-hydroxyalkanoic acid homopolymers consisting of various monomer units, such as $C_4$ hydroxybutanoic acid, $C_5$ hydroxy valeric acid, $C_6$ hydroxyhexanoic acid, $C_7$ hydroxyheptanoic acid, $C_8$ hydroxyoctanoic acid, $C_9$ hydroxynonanoic acid, $C_{10}$ hydroxydecanoic acid and $C_{12}$ hydroxydodecanoic acid.

Particularly, the wild-type poly(3-hydroxyalkanoic acid) synthase (hereafter, sometimes referred to as wild-type enzyme) derived from *Pseudomonas sp.* strain 61-3 can synthesize polyhydroxyalkanoic acid copolymers using intermediate to long chain ($C_{6-14}$) 3-hydroxyalkanoic acids as monomer units as well as poly(hydroxyalkanoic acid) copolymers using $C_4$ 3-hydroxybutanoic acid as monomer units.

The poly(3-hydroxyalkanoic acid) synthase according to the present invention can synthesize poly(hydroxyalkanoic acid) copolymers with high content (composition ratio) of 3-hydroxybutanoic acid compared with the wild-type enzyme. In this way the poly(3-hydroxyalkanoic acid) synthase according to the invention can synthesize copolymeric poly(hydroxyalkanoic acid) with physical properties different from those of the wild-type enzyme.

Particularly the mutant poly(3-hydroxyalkanoic acid) synthase comprising a mutant amino acid sequence of SEQ ID No. 1 in which the serine at position 325 is substituted by cysteine or threonine can synthesize poly(hydroxyalkanoic acid) copolymers with markedly high content of 3-hydroxybutanoic acid compared with the wild-type enzyme. In addition, the mutant poly(3-hydroxyalkanoic acid) synthase comprising a mutant amino acid sequence of SEQ ID No. 1 in which the glutamine at position 481 is substituted by lysine, arginine or methionine can synthesize poly(hydroxyalkanoic acid) copolymers with markedly high content of 3-hydroxybutanoic acid compared with the wild-type enzyme. Moreover, the mutant poly(3-hydroxyalkanoic acid) synthase comprising a mutant amino acid sequence of SEQ ID No. 1 in which the serine at position 477 is substituted by arginine can synthesize poly(hydroxyalkanoic acid) copolymers with markedly high content of 3-hydroxyhexanoic acid compared with the wild-type enzyme.

Moreover, the mutant poly(3-hydroxyalkanoic acid) synthase comprising a mutant amino acid sequence of SEQ ID No. 1 in which the serine at position 325 is substituted by cysteine or threonine and glutamine at position 481 is substituted by lysine, arginine or methionine can synthesize poly(hydroxyalkanoic acid) copolymers with higher content of 3-hydroxybutanoic acid than above.

The gene coding for the mutant poly(3-hydroxyalkanoic acid) synthase according to the present invention is obtained from the gene (hereafter, wild-type gene) coding for the poly(3-hydroxyalkanoic acid) synthase taken from *Pseudomonas sp.* strain 61-3 by inducing a mutation in a given base.

For example, the wild-type gene can be obtained, e.g., by following the method described in Matsusaki, H. et al., J. Bacteriol., 180, 6459-6467 (1998), or by PCR amplification using existing cloned plasmids having $PhaCl_{Ps}$ as template. The so-called site-directed mutagenesis method can be used to change the codon coding for serine at position 325 in the wild-type gene to another codon coding for an amino acid other than serine. Similarly, the site-directed mutagenesis method can also be used to change the codon coding for glutamine at position 481 in the wild-type gene to another codon coding for an amino acid other than glutamine.

Examples of the site-directed mutagenesis methods include, but not limited to, recombinant DNA technology and the PCR method, as follows. For mutagenesis by recombinant DNA technology, for example, if appropriate restriction sites are present on both sides of the target site for mutagenesis in the wild-type gene, the gene is cut at the restriction sites with the restriction enzymes to remove the fragment containing the target mutagenesis site, and another DNA fragment with a mutation at the desired site derived from chemical synthesis and so forth is inserted by the cassette mutagenesis method. For site-directed mutagenesis by the PCR method, a mutation primer containing a desired mutation at a desired site of the wild-type gene and a non-mutant amplification primer containing a sequence at one end of the gene are used to amplify the one side of the gene, a mutation primer having a sequence complementary to the mutation primer above and a non-mutant amplification primer containing a sequence at the other end of the gene are used to amplify the other side, and the two amplification fragments are annealed and subjected to PCR using the above two amplification primers [SHORT PROTOCOLS IN MOLECULAR BIOLOGY, 3rd ed, 1995, F. A. Susubel et al., WILEY].

The gene (hereafter, the mutant 3-hydroxyalkanoic acid synthase gene) encoding the mutant 3-hydroxyalkanoic acid synthase can be linked to an appropriate vector to obtain a recombinant vector that can express in a given host the mutant poly(3-hydroxyalkanoic acid) synthase. In addition, the recombinant vector can be introduced into a given host to develop a transformant that can express the mutant poly(3-hydroxyalkanoic acid) synthase.

Vectors used to insert the 3-hydroxyalkanoic acid synthase gene can be any vectors that are capable of autonomous replication in a given host, including plasmid DNA and phage DNA. For example, if the host is *Escherichia coli*, plasmid DNAs, such as pBR322, pUC18 and pBluescript II, and phage DNAs, such as EMBL 3, M13 and λgt11, if the host is a yeast, YEp13, YCp50, etc., if the host is a plant cell, pBI121, pBI101, etc., and if the host is an animal cell, pcDNAI, pcDNAI/Amp (Invitrogen Corp.), etc., can be used respectively as vectors.

Hosts for recombinant vectors can be any hosts that can polymerize 3-hydroxyalkanoic acid by ester bond to form poly(3-hydroxyalkanoic acid), including, but not limited to, LS series *E. coli* strains such as LS5218 (fadR−), LS1298 (fabB−), LS1300 (fre) and LS6596 (fadA30). These LS series *E. coli* strains are mutant strains in which fadR, a minus regulatory factor for the fatty acid beta-oxidation pathway associated enzyme gene, is destroyed, and can metabolize fatty acids efficiently compared to other *E. coli* bacteria. In addition, ordinary *E. coli* bacteria can be used as a host by inhibiting the fatty acid beta-oxidation pathway with acrylic acid (optimum concentration: 0.24 mg/ml).

Examples of methods for introducing recombinant vectors into bacteria include the method of using calcium ions [Current Protocols in Molecular Biology, Vol. 1, p1.8.1, 1994] and electroporation [Current Protocols in Molecular Biology, Vol. 1, p1.8.4, 1994]. Examples of methods for introducing recombinant vectors into yeast include electroporation [Methods Enzymol., 194,182-187 (1990)], the spheroplast method [Proc. Natl. Acad. Sci. USA, 84, 1929-1933 (1978)] and the lithium acetate method [J. Bacteriol., 153, 163-168 (1983)]. Examples of methods for introducing recombinant vectors into plant cells include the *Agrobacterium* infection method, particle gun method and the polyethylene glycol method. Examples of methods for introducing recombinant vectors into animal cells include the electroporation method and the calcium phosphate method.

The enzymatic activity of the mutant poly(3-hydroxyalkanoic acid) synthase produced in the above transformant can be evaluated, e.g., by culturing the transformant under cultural conditions that allow the production of poly(3-hydroxyalkanoic acid) and examining the intracellular generation/accumulation of poly(3-hydroxyalkanoic acid). In other words, the enzymatic activity of the mutant poly(3-hydroxyalkanoic acid) synthase can be evaluated by comparing the production/accumulation of the poly(3-hydroxyalkanoic acid) between the mutant poly(3-hydroxyalkanoic acid) synthase and the wild-type poly(3-hydroxyalkanoic acid) synthase.

The production/accumulation of poly(3-hydroxyalkanoic acid) can be determined, e.g., by examining the degree of pink coloration of the colony growing on agar plate containing Nile Red specific staining for poly(3-hydroxybutanoate). The intracellular content of the poly(3-hydroxybutanoate), and hence the activity of poly(3-hydroxyalkanoic acid) synthase can be evaluated as higher as the degree of coloration increases. The intensity of fluorescence emitted from radiation with 312-nm light can also be measured for sensitive detection [Spickermann et al. Arch Microbiol., 171: 73-80 (1999)].

In addition, the correct determination of the poly(3-hydroxybutanoate) content in each clone can be done as follows. If the poly(3-hydroxybutanoate) content is about 1% or more by weight on the dried bacterial body basis, poly(3-hydroxybutanoate) is extracted from the bacterial body with an organic solvent (e.g. chloroform), subjected to methanolysis in a methanol-concentrated sulfuric acid solution, and the methylated 3-hydroxybutanoic acid is analyzed by gas chromatography (GC). In addition, if the poly(3-hydroxybutanoate) content is less than about 1% by weight on the dried bacterial body basis, poly(3-hydroxybutanoate) is converted into crotonic acid (elimination reaction) by concentrated sulfuric acid at high temperature, subjected to high-performance liquid chromatography (HPLC) to separate from other components, and absorbance at 210 nm is measured by spectroscopy [Karr et al.: Appl. Environ. Microbiol., 46:1339-1344 (1983); Seebach et al.: Eur. J. Biochem., 224:317-328 (1994)].

In addition, the mutant poly(3-hydroxyalkanoic acid) synthase can be produced by culturing the transformant described above in culture medium to produce/accumulate the mutant poly(3-hydroxyalkanoic acid) synthase in the culture (cultured bacterial body or culture supernatant), which is then collected from the media.

Transformants are cultured in culture medium by conventional methods used for culturing the host. Examples of culture media for culturing transform ants of bacteria such as *E. coli* include complete media or synthetic media, such as LB medium and M9 medium. In addition, transformants are cultured at 37° C. for 12 to 14 hours in an aerobic atmosphere to accumulate intracellularly and recover the mutant poly(3-hydroxyalkanoic acid) synthase.

Carbon sources are necessary for microbial propagation, and include, e.g., carbohydrates such as glucose, fructose, sucrose and maltose. Examples of nitrogen sources include ammonium salts, such as ammonia, ammonium chloride, ammonium sulfate and ammonium phosphate, and peptone, meat extract, yeast extract and corn steep liquor. Examples of inorganic sources include monopotassium phosphate, dipotassium phosphate, magnesium phosphate, magnesium sulfate and sodium chloride. Antibiotics such as kanamycin, ampicillin and tetracycline may be added to the medium as needed, e.g., to provide selection pressure for the retention of plasmid.

Purification of the mutant poly(3-hydroxyalkanoic acid) synthase can be performed by centrifuging the culture to recover (cells are disrupted by a sonicator) and performing affinity chromatography, cation or anion exchange chromatography and gel filtration independently or in combination. Whether the purified material is the desired enzyme or not can be determined by conventional methods, such as SDS polyacrylamide gel electrophoresis and western blotting.

Biodegradable polyester with desired physical properties can be produced by culturing the transformant described above in appropriate medium. The properties of the biodegradable polyester obtained are different from those of the biodegradable polyester derived from the wild-type enzyme because it is biosynthesized using the mutant poly(3-hydroxyalkanoic acid) synthase.

Examples of biodegradable polyesters include a copolymer of 3-hydroxybutanoic acid (3HB) and 3-hydroxyalkanoic acid (3HA), such as a copolymer of 3HB and 3-hydroxyhexanoic acid (3HHx). Hereinafter, a copolymer of 3HB and 3HA may be described as "P(3HB-co-3HA)", and a copolymer of 3HB and 3HHx as "P(3HB-co-3HHx)."

P(3HB-co-3HA) can be produced by culturing the transformant described above in a suitable culture medium. For example, if the host is *E. coli* LS5218, P(3HB-co-3HHx) is produced inside the bacterial cells.

In the case of the transformant above, P(3HB-co-3HA) is accumulated in large quantities, and unlike the case where the wild-type enzyme is used, the 3-hydroxybutanoic acid content (composition ratio) in P(3HB-co-3HA) increases significantly. Due to the high composition ratio of 3HB, the P(3HB-co-3HA) becomes more rigid, showing superior practical characteristics.

Following the method by Kato et al. [Kato, M. et al., Appl. Microbiol. Biotechnol. 45, 363 (1996); Kato, M. et al., Bull. Chem. Soc. Jpn. 69, 515 (1996)], the intracellular content of accumulated polyesters and their compositions can be determined by extracting them from the cells with organic solvents such as chloroform and subjecting the extract to analyses by gas chromatography, NMR, and so forth.

This patent specification encompasses the contents of the specification and/or figures of JP Patent Application No. 2002-154374, which is the basis for priority of the present application.

BEST MODE FOR CARRYING OUT THE INVENTION

The following specific examples illustrate the present invention, but are not intended to limit the scope of the invention. The following example shows a case in which a mutant poly(3-hydroxyalkanoic acid) synthase of the invention was obtained using so-called evolutionary technologies. However, the following examples are not intended to limit the technical scope of the present invention. That is, the methods for obtaining the mutant poly(3-hydroxyalkanoic acid) synthase of the invention are not limited to the following examples.

EXAMPLE 1

Figure 1:
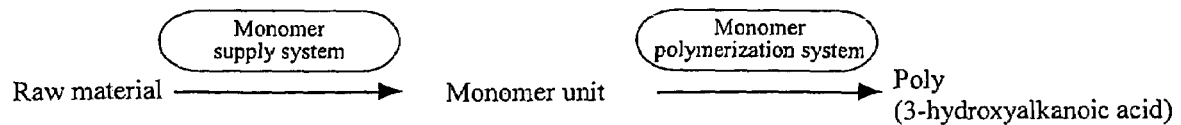
FIG. 1 is a view of a biosynthesis scheme of poly(3-hydroxyalkanoic acid)
Figure 2:
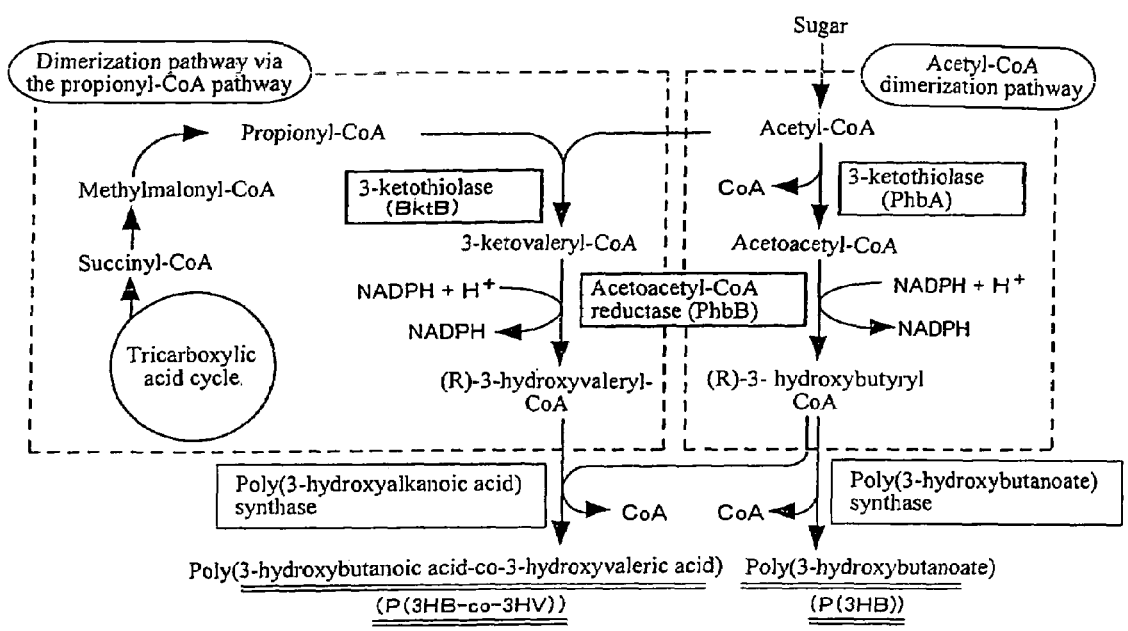
FIG. 2 is a view showing the production of polyester by the acetyl-CoA dimerization system in bacteria and the enzymes involved.
Figure 3:
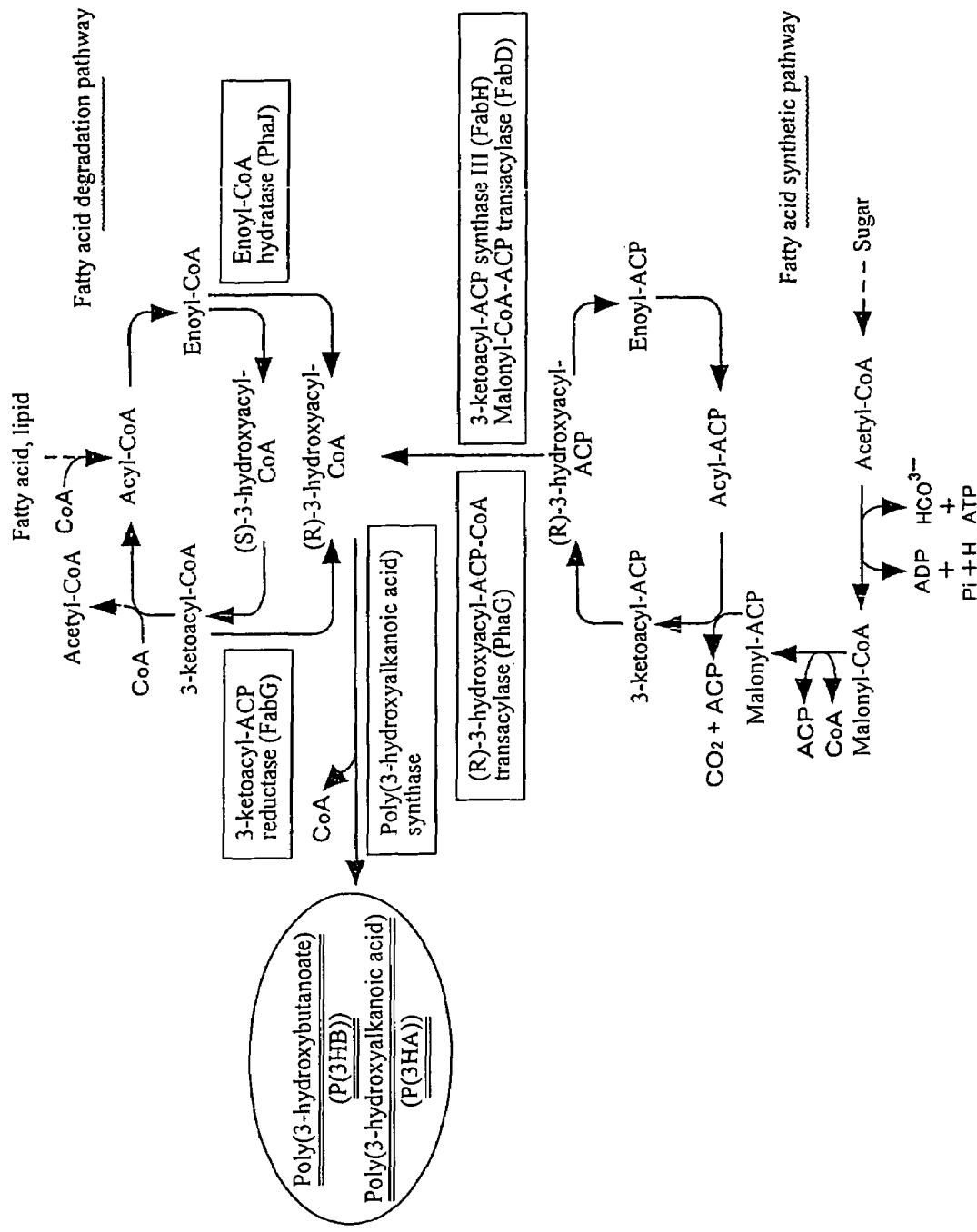
FIG. 3 is a view showing the production of polyester by the fatty acid metabolic system in bacteria and the enzymes involved.
Figure 4:
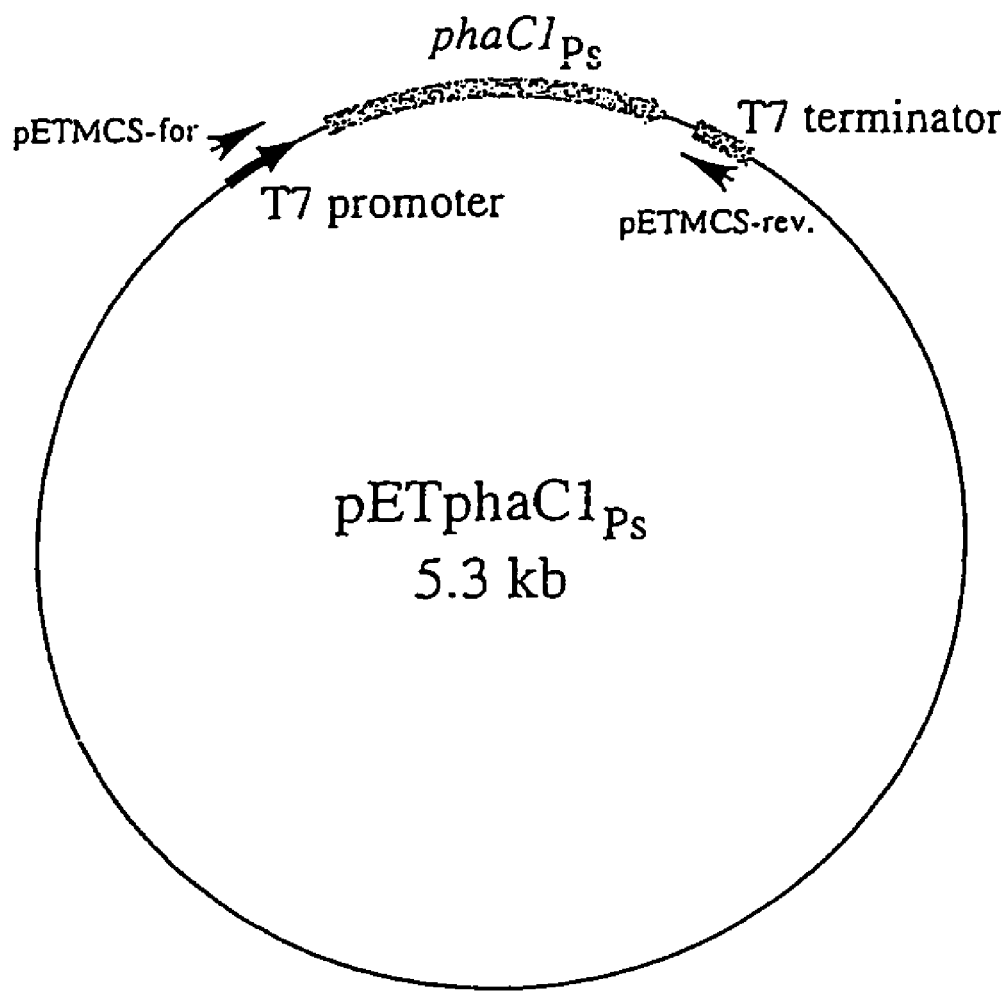
FIG. 4 is a schematic diagram of the plasmid vector pETphaCl$_{Ps}$.

Modification of the poly(3-hydroxyalkanoic acid) synthase by the error-prone PCR method Random mutation was introduced into the entire region of the gene (PhaCl$_{Ps}$) encoding the poly(3-hydroxyalkanoic acid) synthase derived from *Pseudomonas sp.* strain 61-3 by the error-prone PCR method. For the error-prone PCR method, the plasmid vector pETphaCl$_{Ps}$ (FIG. 4) containing PhaCl$_{Ps}$ was used as template, and the forward primer pET-MCS-for.: 5'-CCCAACGCTGCCCGAGATCTCGATC-CCGCG-3' (SEQ ID No. 2) corresponding to the upstream side of the multi-cloning site of the basic vector pET-23a(+) and the reverse primer pETMCS-rev.: 5'-AGCTTC-CTTTCGGGCTTTGTTAGCAGCCGG-3' (SEQ ID No. 3) corresponding to the downstream side of the multi-cloning site of the basic vector pET-23a(+) were used. In the error-prone PCR method, the introduction of mutations into the entire PhaCl$_{Ps}$ region was tried without limiting locations for mutation by performing PCR under conditions that reduce the fidelity of polymerase to incorporate substrate.

pET-23a(+) (Novagen Corp.) was used as the basic vector for pETphaCl$_{Ps}$. PhaCl$_{Ps}$ amplification was performed by the PCR method using pBSEX22 (Matsusaki, H. et. al., J. Bacteriology. 180, 6459 (1998)) as a template, and using a primer containing the restriction site (CATATG) for the restriction enzyme NdeI so as to overlap with the start codon (ATG) of PhaCl$_{Ps}$ and a primer in which the restriction site (GGATCC) for the restriction enzyme BamHI was introduced downstream of the termination codon of PhaCl$_{Ps}$. Subsequently, the PCR-amplified DNA fragments were purified and isolated, and were digested by NdeI and BamHI. Subsequently, the DNA fragments digested with the restriction enzymes were inserted by replacement into the same restriction site of the basic plasmid vector pET-23a(+) to obtain pETphaCl$_{Ps}$ having the wild-type PhaCl$_{Ps}$.

In the error-prone PCR method, the reaction solution was prepared so as to achieve the composition shown in Table 1.

TABLE 1

| | |
|---|---|
| 100 mM Tris-HCl (pH 8.8) | 10 μl |
| 500 mM KCl | 10 μl |
| 1 mg/ml BSA | 10 μl |
| 50 mM MgCl$_2$ | 10 μl |
| 10 mM dATP | 2 μl |
| 10 mM dGTP | 2 μl |
| 10 mM dCTP | 2 μl |
| 10 mM dTTP | 2 μl |
| pBSEE32phbAB (Ca. 5 ng) | 10 μl |
| forward and reverse primer (10 μl) | 5 μl each |
| DMSO | 10 μl |
| TaKaRa Taq DNA polymerase | 0.5 μl |
| ddH$_2$O | 21.5 μl |
| Total | 100 μl |

The temperature cycle of the error-prone PCR method consisted of thermal denaturation at 94° C. for one minute, annealing at 50° C. for one minute and elongation reaction at 72° C. for two minutes, and this cycle was repeated 25 times. The Gene Amp PCR system 9700 (Perkin-Elmer Applied Biosystems) was used for the error-prone PCR method.

Figure 5:
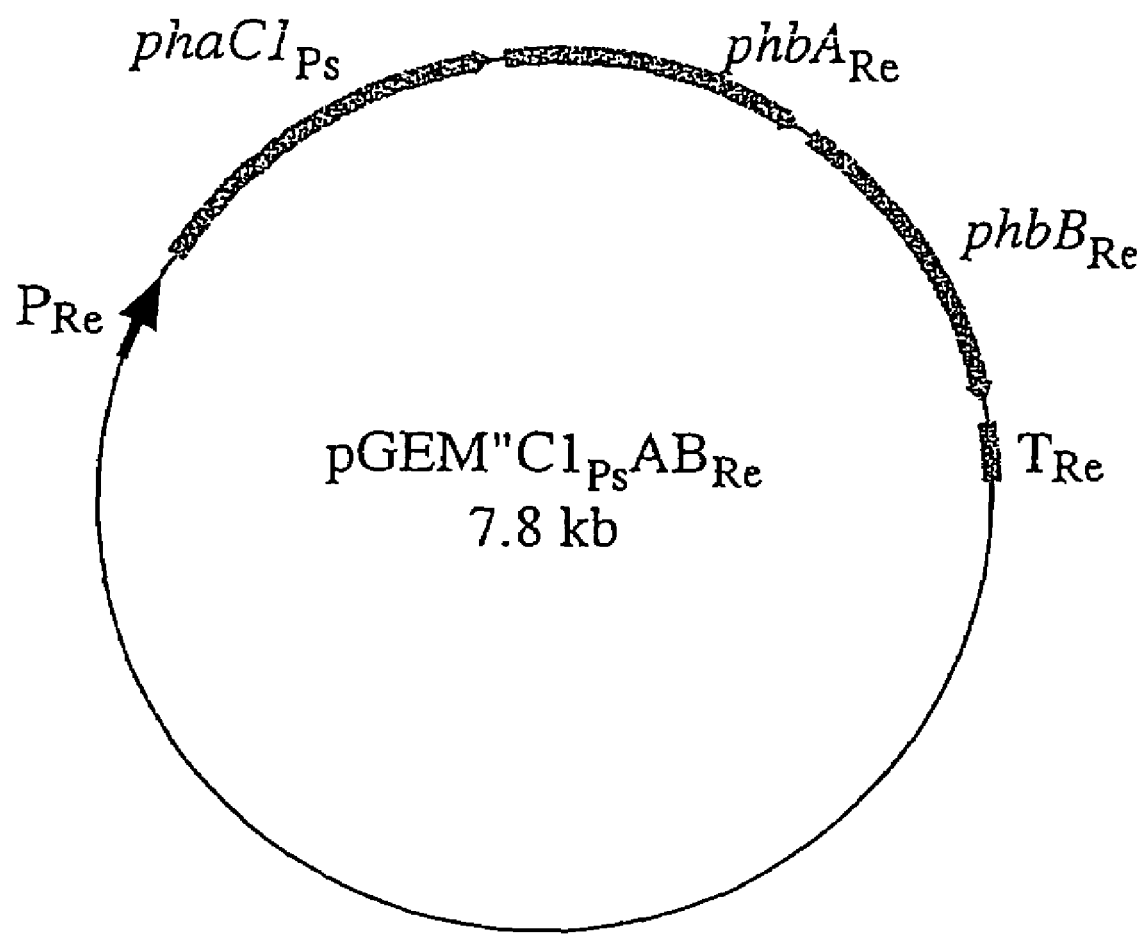
FIG. 5 is a schematic diagram of the plasmid vector pGEM"Cl$_{Ps}$AB$_{Re}$.

Subsequently, the DMA fragments amplified by the error-prone PCR method were purified and isolated, and were digested by XbaI and BamHI. Subsequently, the DNA fragments digested with the restriction enzymes were inserted by replacement in between the XbaI and BglII restriction sites of the monomer-supplying gene expression plasmid pGEM-"AB$_{Re}$ to obtain a molecular assemblage (pool of mutant clones) of mutant PhaCl$_{Ps}$. The plasmid vector obtained was referred to as pGEM"ClPsAB$_{Re}$ (FIG. 5).

pGEM"AB$_{Re}$ was constructed by insertion of the phb operon promoter derived from Ralstonia eutropha, the β-ketothiolase gene (phbA$_{Re}$), the acetoacetyl-CoA reductase gene (phbB$_{Re}$) and the terminator of the phb operon in this order into the multi-cloning site of a basic vector pGEM-T (Promega Corp.). These phb operon promoter, β-ketothiolase gene (phbA$_{Re}$), acetoacetyl-CoA reductase gene (phbB$_{Re}$) and the phb operon terminator were obtained by digesting the plasmid vector pGEM'-phbCAB$_{Re}$ described in Matsusaki, H. et. al., J. Bacteriol., 180, 6459-6467 (1998) with restriction enzymes.

The plasmid vector pGEM"Cl$_{Ps}$AB$_{Re}$ obtained is an assemblage of mutant PhaCl$_{Ps}$ molecules, and includes various types of PhaCl$_{Ps}$ into which mutations were introduced at random over the entire region. Next, pGEM"Cl$_{Ps}$AB$_{Re}$ was incorporated into competent cells of Escherichia coli JM109 strains by transformation. The cells subjected to transformation were incubated at 37° C. for 14 hours on LB agar media containing Nile Red, which is capable of specific staining of poly(3-hydroxybutanoate), glucose and ampicillin (0.5 μg/ml Nile Red, 2% glucose, 50 μg/ml ampicillin, 1% trypton, 0.5% yeast extract and 1% NaCl, pH 7.0) to select transformed cells, and the poly(3-hydroxybutanoate) production/accumulation in each transformed cell was estimated from the degree of pink coloration.

As a result, of the 133,671 clones formed on the LB agar media, 121 clones developed light pink color. HPLC was used to analyze the PHB content in these 121 clones. Prior to analysis by HPLC, clones were subjected to treatment with concentrated sulfuric acid to change the intracellular PHB into crotonic acid.

Specifically, bacterial cells were incubated at 30° C. for 96 hours, harvested with a 1.5-ml microtube, frozen, and freeze-dried. After weighing the dried bacterial body, the PHB in the bacterial body was converted to crotonic acid with concentrated sulfuric acid. For crotonic acid conversion, 1 ml of concentrated sulfuric acid was added to the dried bacterial body in the microtube, and the mixture was heated to 120° C. for 40 minutes and quenched on ice. As a result of this procedure, dehydration reaction was induced by concentrated sulfuric acid at high temperature, and the bacterial PHB was converted into crotonic acid.

Next, the cooled sample was diluted with four parts of 0.014 N sulfuric acid solution, cooled and used as an HPLC sample. The sample was filtered through 0.45-μm hydrophilic PVDF membrane, and 10 μl of the filtrate was injected into the HPLC system. The HPLC system used was Shimadzu LC-10Avp system. The column used was Bio-rad Aminex HPX-87H (300×7.8 mm), which is a cation-exchange resin column of styrene divinylbenzene copolymer of a degree of crosslinking of 8%. In addition, Bio-rad Cation-H Refill Cartridge (30×4.6 mm) was used as the guard column. The mobile phase was 0.014 N sulfuric acid solution with a flow rate of 0.7 ml/min. The column temperature was set at 60° C., and the 210-nm absorbance of the carbonyl group of crotonic acid produced by dehydration reaction was detected spectroscopically. The retention time of crotonic acid was 20.4 minutes. The PHB accumulation rate was calculated from the relational expression (working curve) between the quantity of crotonic acid and area.

Results of measurement of PHB accumulation in 121 clones using an HPLC system show that 18 clones had higher PHB accumulation than the wild-type PhaCl$_{Ps}$ expression strain. The wild-type PhaCl$_{Ps}$ expression strain was prepared in the same way as above except that the wild-type PhaCl$_{Ps}$ was used. Results of sequencing of all 18 mutants show that 7 mutants had single mutation, 9 had double mutations, and 2 had triple mutations. Sequencing was performed by the dideoxy linkage termination method using a Prism 310 DNA sequencer or a Prism 377 DNA sequencer with a BigDye terminator cycle sequencing ready reaction kit (Applied Biosystems Corp.). The base sequence information provided from sequencing was analyzed with GENETYX-MAC software (Software Development Corp.) or BLAST (Basic Local Alignment Search Tool; offered by National Center for Biotechnology Information). It was decided to carry out site-specific saturation mutagenesis on the amino acid replacement mutants that had significantly increased PHB content.

Figure 6:
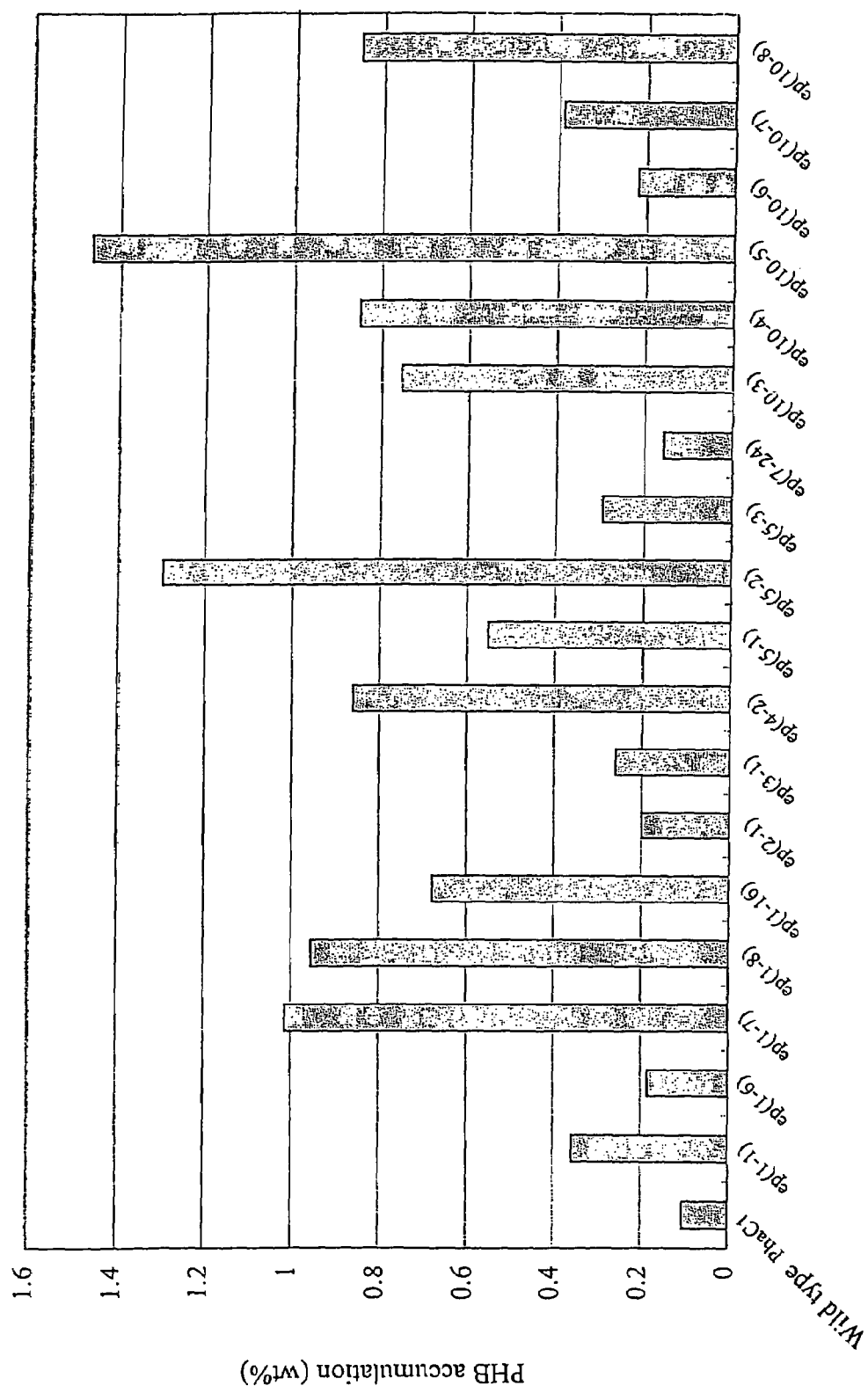
FIG. 6 is a characteristic diagram showing the results of PHB accumulation in 18 clones with greater PHB accumulation than that for the wild-type PhaCl$_{Ps}$ expression strain, and the wild-type PhaCl$_{Ps}$ expression strain.

The results of PHB accumulation in the 18 clones with greater PHB accumulation than that for the wild-type PhaCl$_{Ps}$ expression strain, and the wild-type PhaCl$_{Ps}$ expression strain are shown in FIG. 6. In FIG. 6, the ordinate represents PHB accumulation and the abscissa represents clone names.

In addition, pGEM"Cl$_{Ps}$AB$_{Re}$ was extracted from these 18 clones to determine the base sequence of PhaCl$_{Ps}$ to identify mutation sites. In addition, the amino acid mutations in PhaCl$_{Ps}$ were analyzed based on the mutation sites identified. The relation between the PHB accumulation in each clone shown in FIG. 6 and the amino acid mutations is shown in Table 2.

TABLE 2

| Mutant (amino acid substitution) | PHB content (wt %) |
|---|---|
| Wild strain | 0.102 |
| 1-1 (R27H/S477R) | 0.358 |
| 1-6 (E130D/L327F) | 0.182 |
| 1-7 (Q481R) | 1.011 |
| 1-8 (N16T/M292V/S325T) | 0.953 |
| 1-16 (S325C) | 0.764 |
| 2-1 (Q12R/M362L/S497G) | 0.198 |
| 3-1 (A304V/M369L) | 0.259 |

TABLE 2-continued

| Mutant (amino acid substitution) | PHB content (wt %) |
| --- | --- |
| 4-2 (S325C/H350Y) | 0.86 |
| 5-1 (E115K/S325C) | 0.551 |
| 5-2 (Q481R) | 1.294 |
| 5-3 (S477R/S547T) | 0.295 |
| 7-24 (D30N/N247Y) | 0.155 |
| 10-3 (Q481R) | 0.753 |
| 10-4 (L20P/Q481R) | 0.849 |
| 10-5 (N5D/Q481K) | 1.461 |
| 10-6 (S477R) | 0.219 |
| 10-7 (E130D) | 0.388 |
| 10-8 (Q481R) | 0.85 |

EXAMPLE 2

In Example 2, amino acid mutations that may be attributed to the increase in PHB accumulation from the results in FIG. 6 and Table 2 were considered. First, from the results shown in FIG. 6 and Table 2, it was thought that the amino acid replacements at serine at position 325 and glutamine at position 481 affected the increase in PHB accumulation in the 18 clones that showed higher PHB accumulation than the wild-type PhaCl$_{Ps}$ expression strain.

Therefore, site-specific saturation mutagenesis at the 325th and 481st positions was tried which showed mutations that caused a significant increase in the PHB content. First, serine at position 325 was substituted by an amino acid other than serine, and the effect of the substitution on PHB accumulation was examined. Concretely, a primer for introducing mutation was first designed so as to change the codon coding for serine at position 325 to another codon coding for an amino acid other than serine. Next, PhaCl$_{Ps}$ was prepared in which serine at position 325 was substituted by a given amino acid by site-directed mutagenesis using the primer for introducing mutation. In other words, 19 types of PhaCl$_{Ps}$ were prepared which encoded poly(3-hydroxyalkanoic acid) synthase in which the 325-position amino acid was substituted by any one of the 19 amino acids other than serine. These 19 types of PhaCl$_{Ps}$ were inserted into the pGEM"AB$_{Re}$ described above.

Figure 7:
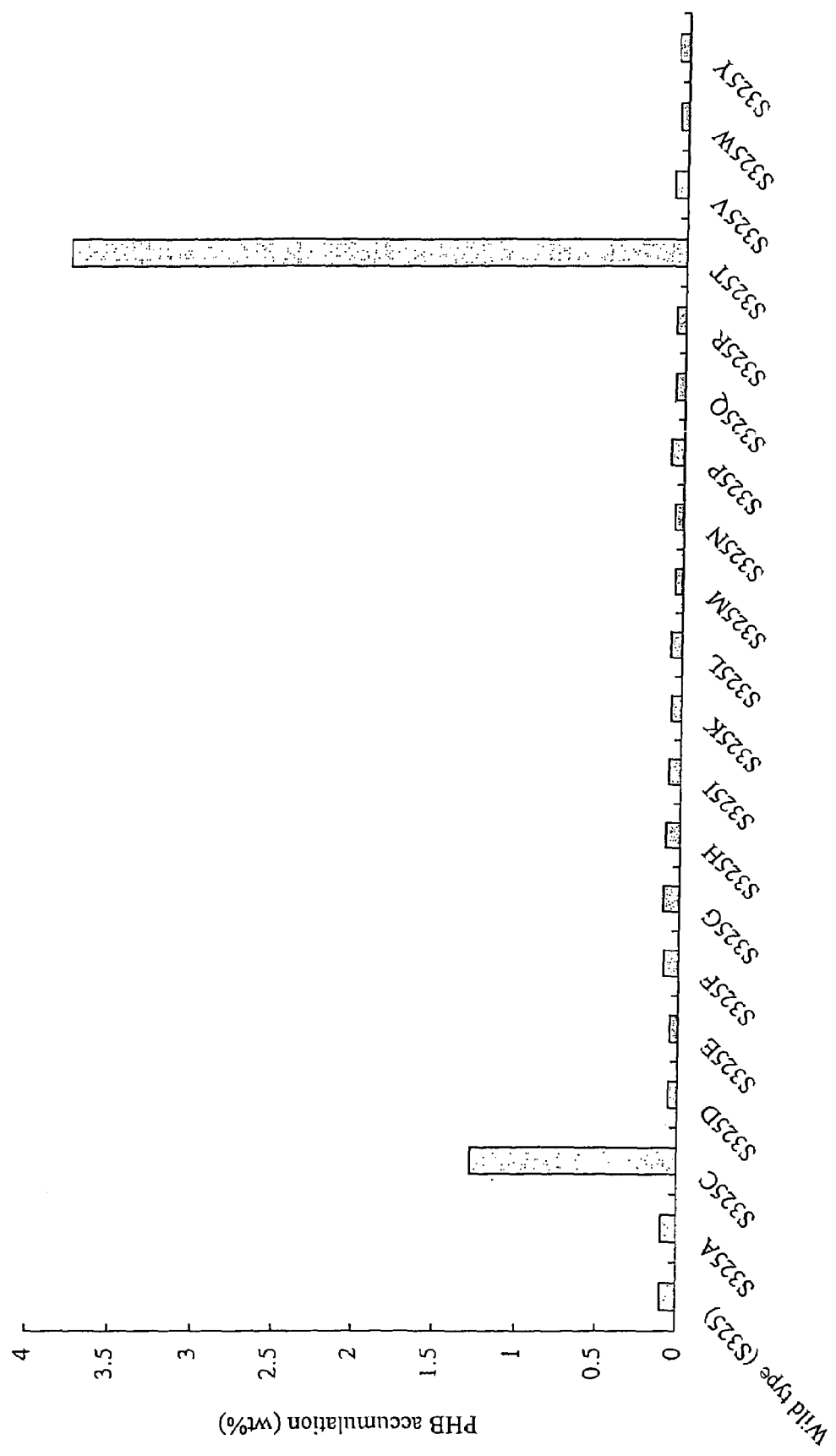
FIG. 7 is a characteristic diagram showing the results of PHB accumulation in a mutant PhaCl$_{Ps}$ expression strain in which the 325-position amino acid is mutated, and the wild-type PhaCl$_{Ps}$ expression strain.

Next, these 19 types of PhaCl$_{Ps}$ were incorporated into the competent cells of *E. coli* JM109 by transformation. As in Example 1, PHB accumulation in transformed cells was measured. FIG. 7 shows the results of PHB accumulation in 19 types of PhaCl$_{Ps}$ expression strains and the wild-type PhaCl$_{Ps}$ expression strain. In FIG. 7, the ordinate represents PHB accumulation and the abscissa represents mutant types. The relation between the PHB accumulation in each mutant shown in FIG. 7 and the amino acid mutations is shown in Table 3.

TABLE 3

| | PHB content (wt %) |
| --- | --- |
| Wild strain | 0.102 |
| S325A | 0.101 |
| S325C | 1.277 |
| S325D | 0.059 |
| S325E | 0.05 |
| S325F | 0.096 |
| S325G | 0.101 |
| S325H | 0.092 |
| S325I | 0.075 |
| S325K | 0.066 |

TABLE 3-continued

| | PHB content (wt %) |
| --- | --- |
| S325L | 0.074 |
| S325M | 0.051 |
| S325N | 0.058 |
| S325P | 0.084 |
| S325Q | 0.06 |
| S325R | 0.059 |
| S325T | 3.785 |
| S325V | 0.081 |
| S325W | 0.05 |
| S325Y | 0.063 |

The results in FIG. 7 and Table 3 show that the mutant poly(3-hydroxyalkanoic acid) synthase in which serine at position 325 of the original synthase is substituted by cysteine or threonine has quite high PHB accumulation compared with the wild-type poly(3-hydroxyalkanoic acid) synthase. This shows that these mutant poly(3-hydroxyalkanoic acid) synthases can be used to obtain P(3HB-co-3HA) having different composition ratios than that from the wild-type poly(3-hydroxyalkanoic acid) synthase. Particularly, these mutant poly (3-hydroxyalkanoic acid) synthases can be used to obtain P(3HB-co-3HA) having high 3HB ratios compared to the P(3HB-co-3HA) from the wild-type poly(3-hydroxyalkanoic acid) synthase.

Figure 8:
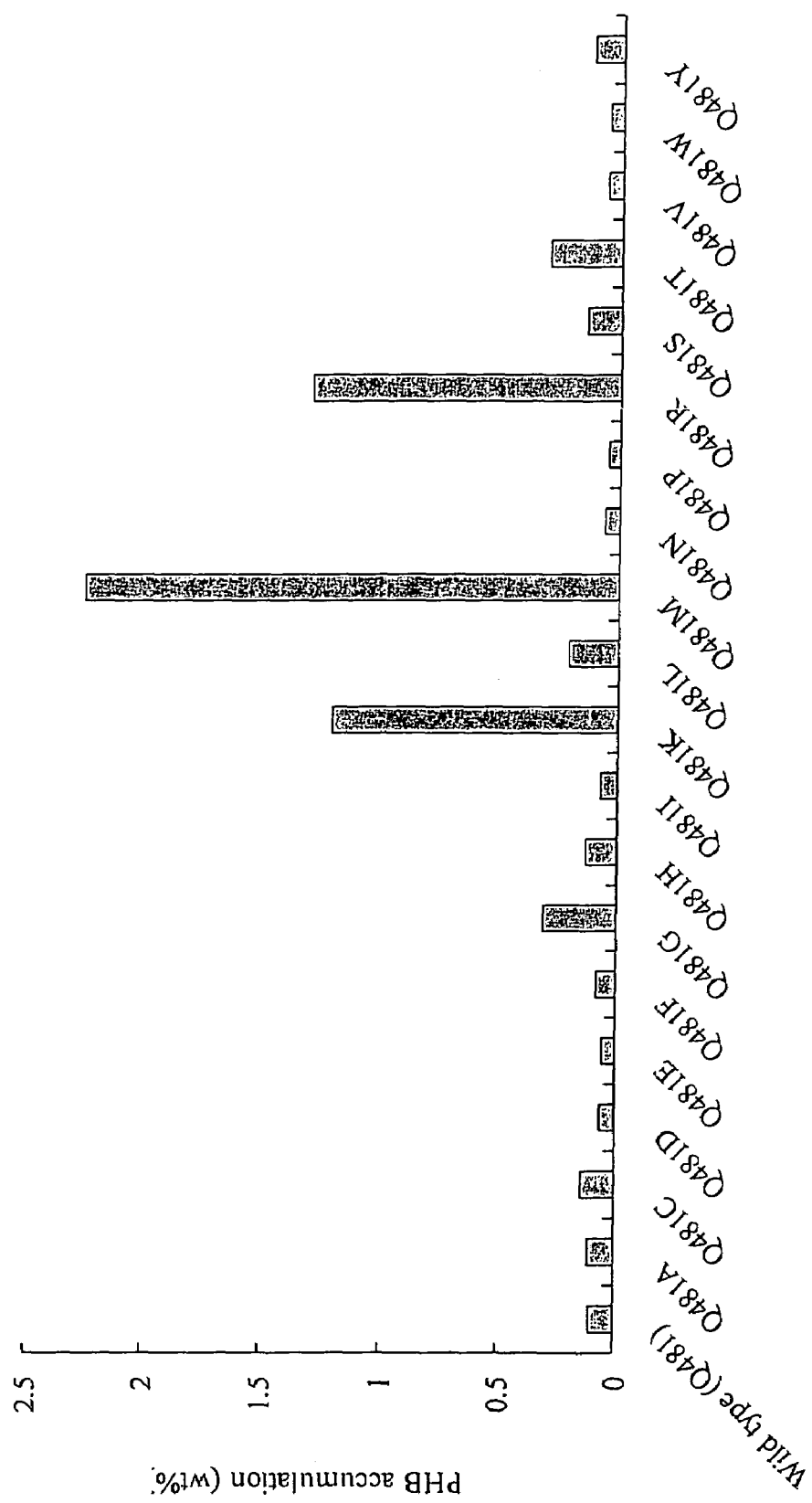
FIG. 8 is a characteristic diagram showing the results of PHB accumulation in a mutant PhaCl$_{Ps}$ expression strain in which the 481-position amino acid is mutated, and the wild-type PhaCl$_{Ps}$ expression strain.

Next, glutamine at position 481 was substituted by an amino acid other than glutamine, and the effect of the substitution on PHB accumulation was examined following the procedure above employed when serine at position 325 was substituted by an amino acid other than serine. FIG. 8 shows the results of PHB accumulation in the 19 types of PhaCl$_{Ps}$ expression strains in which glutamine at position 481 was substituted by an amino acid other than glutamine, and the wild-type PhaCl$_{Ps}$ expression strain. In FIG. 8, the ordinate represents PHB accumulation and the abscissa represents mutation types. The relation between the PHB accumulation in each mutant shown in FIG. 8 and the amino acid mutations is shown in Table 4.

TABLE 4

| | PHB content (wt %) |
| --- | --- |
| Wild strain | 0.102 |
| Q481A | 0.109 |
| Q481C | 0.143 |
| Q481D | 0.062 |
| Q481E | 0.052 |
| Q481F | 0.08 |
| Q481G | 0.308 |
| Q481H | 0.131 |
| Q481I | 0.065 |
| Q481K | 1.201 |
| Q481L | 0.211 |
| Q481M | 2.248 |
| Q481N | 0.064 |
| Q481P | 0.047 |
| Q481R | 1.296 |
| Q481S | 0.139 |
| Q481T | 0.301 |
| Q481V | 0.058 |
| Q481W | 0.051 |
| Q481Y | 0.12 |

The results in FIG. 8 and Table 4 show that the mutant poly(3-hydroxyalkanoic acid) synthase in which glutamine at position 481 of the original synthase is substituted by glycine, lysine, leucine, methionine, arginine, serine or threonine has quite high PHB accumulation compared with the wild-type poly(3-hydroxyalkanoic acid) synthase. The mutant poly(3-hydroxyalkanoic acid) synthase in which glutamine at position 481 is substituted by lysine, arginine or methionine, in particular, showed markedly increased PHB accumulation.

This shows that these mutant poly(3-hydroxyalkanoic acid) synthases can be used to obtain P(3HB-co-3HA) having different composition ratios than that from the wild-type poly (3-hydroxyalkanoic acid) synthase. Particularly, these mutant poly(3-hydroxyalkanoic acid) synthases can be used to obtain P(3HB-co-3HA) having high 3HB ratios compared to the P(3HB-co-3HA) from the wild-type poly(3-hydroxyalkanoic acid) synthase.

In addition, the mutant poly(3-hydroxyalkanoic acid) synthases contained in the clones that showed higher PHB accumulations in FIGS. 7 and 8 and Tables 3 and 4 can be used to obtain P(3HB-co-3HA) having higher 3HB ratios. This further shows that the evolutionary technology adopted this time was very effective in locating mutations conferring high substrate specificity for these 3HB substrates.

Figure 9:
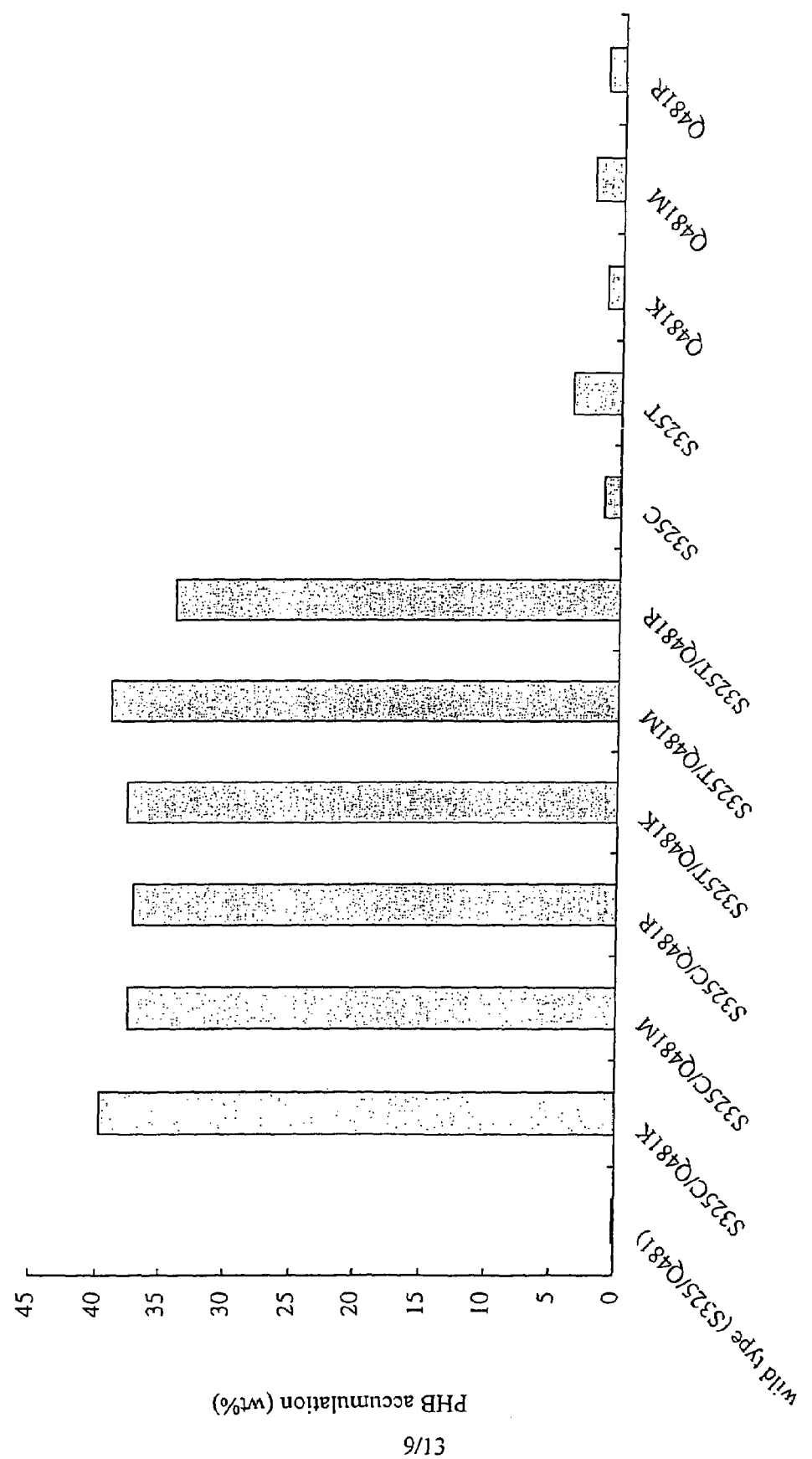
FIG. 9 is a characteristic diagram showing the results of PHB accumulation in a mutant PhaCl$_{Ps}$ expression strain in which the 325- and 481-position amino acids are mutated, and the wild-type PhaCl$_{Ps}$ expression strain.

As favorable mutations were identified which were involved in modifications of substrate specificity and increased PHA content, next-generation evolution was explored. Combinations (a total of six types of double mutations) of favorable mutations at 325-position (S325T and S325C) and 481-position (Q481K, Q481R and Q481M) were prepared by means of genetic engineering. Tables 5 and 6 show PHB accumulations in the PhaCl$_{Ps}$ expression strains having one of the substitutions at the 130-, 477-, 325- and 481-positions, which the results from Example 1 suggest may increase PHB accumulation, PhaCl$_{Ps}$ expression strains having combinations of these mutations (double mutations, triple mutations and quadruple mutations), and the wild-type PhaCl$_{Ps}$ expression strain. In addition, PhaCl$_{Ps}$ expression strains having one of S325T, S325C, Q481K, Q481R and Q481M, among others shown in Table 5, and PhaCl$_{Ps}$ expression strains having combinations of these are shown in FIG. 9. In FIG. 9, the ordinate represents PHB accumulation and the abscissa represents mutation types.

TABLE 5

|  |  | PHB accumulation (wt %) |
|---|---|---|
|  | Wild-type enzyme | 0.102 |
| Single mutation | E130D | 1.012 |
|  | S325C | 1.277 |
|  | S325T | 3.785 |
|  | S477R | 0.486 |
|  | Q481K | 1.201 |
|  | Q481M | 2.248 |
|  | Q481R | 1.296 |
| Double mutation | E130D/S325C | 37.630 |
|  | E130D/S325T | 39.320 |
|  | E130D/S477R | 5.556 |
|  | E130D/Q481K | 33.047 |
|  | E130D/Q481M | 33.934 |
|  | E130D/Q481R | 28.766 |
|  | S325C/S477R | 36.865 |
|  | S325T/S477R | 36.010 |
|  | S325C/Q481K | 37.792 |
|  | S325C/Q481M | 39.116 |
|  | S325C/Q481R | 34.148 |
|  | S325T/Q481K | 39.850 |
|  | S325T/Q481M | 37.595 |
|  | S325T/Q481R | 37.262 |

TABLE 6

|  |  | PHB accumulation (wt %) |
|---|---|---|
|  | Wild-type enzyme | 0.102 |
| Triple mutation | E130D/S325C/S477R | 42.148 |
|  | E130D/S325T/S477R | 43.036 |
|  | E130D/S325C/Q481K | 39.463 |
|  | E130D/S325C/Q481M | 38.223 |
|  | E130D/S325C/Q481R | 38.486 |
|  | E130D/S325T/Q481K | 38.637 |
|  | E130D/S325T/Q481M | 39.458 |
|  | E130D/S325T/Q481R | 37.256 |
|  | E130D/S477R/Q481K | 3.423 |
|  | E130D/S477R/Q481M | 25.420 |
|  | E130D/S477R/Q481R | 2.834 |
|  | S325C/S477R/Q481K | 8.433 |
|  | S325C/S477R/Q481M | 39.353 |
|  | S325C/S477R/Q481R | 6.095 |
|  | S325T/S477R/Q481K | 39.020 |
|  | S325T/S477R/Q481M | 40.700 |
|  | S325T/S477R/Q481R | 38.900 |
| Quadruple mutation | E130D/S325C/S477R/Q481K | 39.474 |
|  | E130D/S325C/S477R/Q481M | 42.182 |
|  | E130D/S325C/S477R/Q481R | 39.706 |
|  | E130D/S325T/S477R/Q481K | 45.943 |
|  | E130D/S325T/S477R/Q481M | 42.046 |
|  | E130D/S325T/S477R/Q481R | 41.969 |

Results in FIG. 9 and Tables 5 and 6 show that PhaCl$_{Ps}$ expression strains having one of the substitutions at positions 130, 477, 325 and 481 and PhaCl$_{Ps}$ expression strains having combinations of these mutations (double mutations, triple mutations and quadruple mutations) accumulate quite high PHB compared to the wild-type PhaCl$_{Ps}$ expression strain. In addition, double-mutation, triple-mutation and quadruple-mutation PhaCl$_{Ps}$ expression strains showed quite high PHB accumulations compared to single-mutation PhaCl$_{Ps}$ expression strains. Particularly, mutant poly(3-hydroxyalkanoic acid) synthases in which serine at position 325 is substituted by cysteine or threonine and glutamine at position 481 is substituted by lysine, arginine or methionine, can be used to obtain P(3HB-co-3HA) having higher 3HB ratios than the P(3HB-co-3HA) from the wild-type poly(3-hydroxyalkanoic acid) synthase. This resulted in a synergistic effect of favorable mutations (effects of the substitutions at serine at position 325 and glutamine at position 481), increasing the PHB content remarkably (38% on average) compared to the individual single mutations.

This mapping may have located the amino acid residues involved in determining substrate specificity. Thus, this method has been shown to have the possibility, as amino acid residues involved in other substrate specificity are located, of creating various favorable mutant enzymes by combining the amino acid substitutions at such locations.

EXAMPLE 3

In Example 3, mutant PhaCl$_{Ps}$ contained in each of the clones ep(1-1), ep(1-8), ep(1-16), ep(4-2), ep(10-3), ep(10-4) and ep(10-5) of the 18 clones obtained in Example 1 was used to transform *E. coli* LS5218, and P(3HB-co-3HA) copolymer accumulation in transformed *E. coli* LS5218 cells and the monomer compositions of P(3HB-co-3HA) were analyzed. *E. coli* LS5218 can synthesize P(3HB-co-3HA) copolymer from dodecanoic acid. *E. coli* LS5218 was obtained from *E. coli* Genetic Stock Center (Accession No. CGSC 6966).

First, for each of the clones ep(1-1), ep(1-8), ep(1-16), ep(4-2), ep(10-3), ep(10-4) and ep(10-5) obtained in Example 1, a plasmid vector pGEM"Cl$_{Ps}$AB$_{Re}$ containing mutant PhaCl$_{Ps}$ was purified according to the method by Miller et al.

Figure 10:
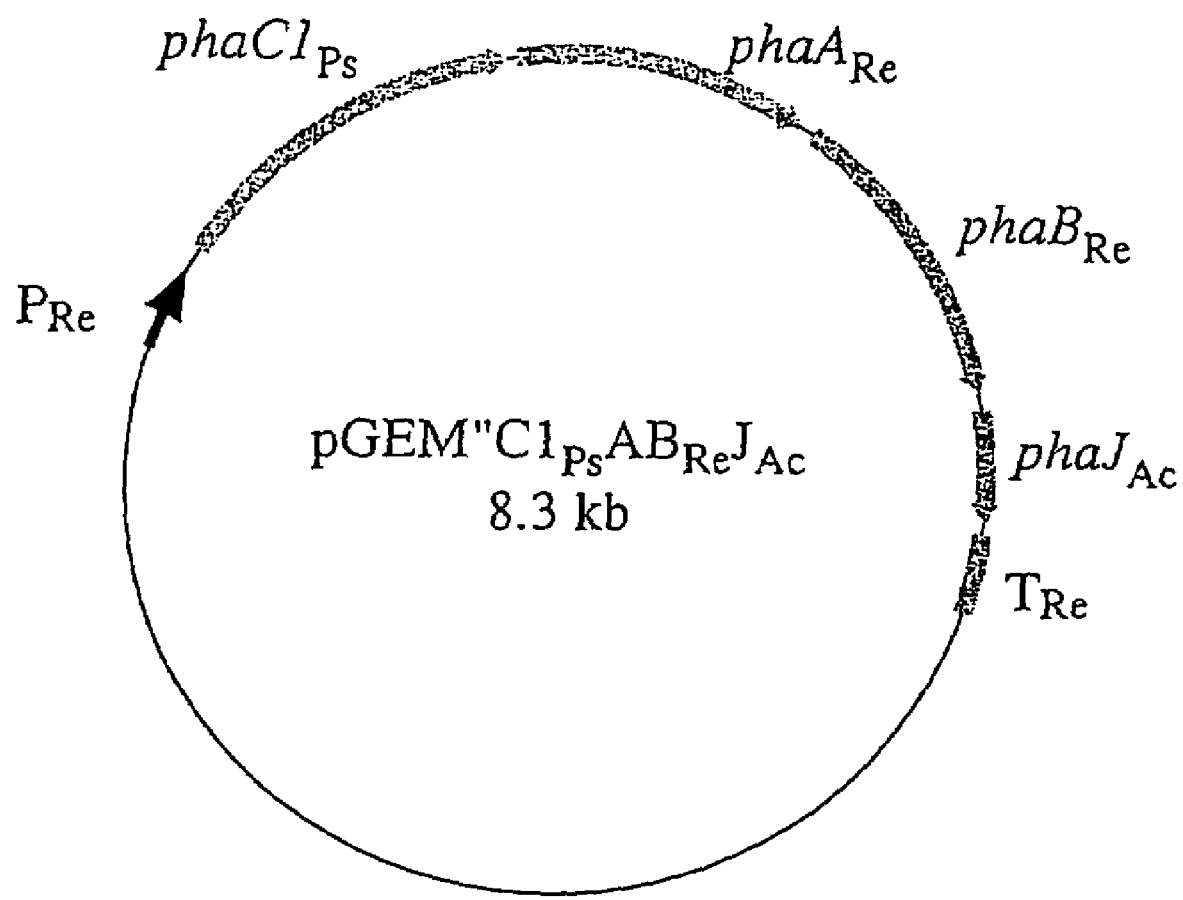
FIG. 10 is a schematic diagram of the plasmid vector pGEM"Cl$_{Ps}$AB$_{Re}$J$_{Ac}$.

Next, the purified plasmid vectors were digested with the restriction enzymes XbaI and PstI, and DNA fragments containing mutant PhaCl$_{Ps}$ were purified. Subsequently, the purified DNA fragments were inserted by replacement in between the XbaI and PstI restriction sites of the monomer-supplying gene expression plasmid pGEM"AB$_{Re}$J$_{Ac}$ to obtain a plasmid vector for synthesizing the p(3HB-co-3HA) copolymer. The plasmid vector obtained was referred to as pGEM"Cl$_{Ps}$AB$_{Re}$-J$_{Ac}$ (FIG. 10).

The plasmid vector pGEM"AB$_{Re}$J$_{Ac}$ is a mutant of pGEM-"AB$_{Re}$ used in Example 1, in which the (R)-specific enoyl CoA hydratase gene (phaJ$_{Ac}$) derived from *Aeromonas caviae* is inserted downstream of its phbB$_{Re}$. The (R)-specific enoyl CoA hydratase gene (phaJ$_{Ac}$) was obtained by digesting the plasmid vector pETNB3 described in Fukui, T. et. al., J. Bacteriol., 180, 667 (1998) with restriction enzymes.

Next, the purified plasmid vector pGEM"Cl$_{PS}$AB$_{Re}$J$_{Ac}$ was used to transform *E. coli* LS5218. The transformed *E. coli* LS5218 was incubated at 37° C. for 72 hours in M9 culture medium containing 0.5% dodecanoic acid and 50 μg/ml ampicillin. The composition of the M9 culture medium is shown in Table 7.

TABLE 7

| | |
|---|---|
| Na$_2$HPO$_4$•12H$_2$O | 17.4 g |
| KH$_2$PO$_4$ | 3 g |
| NaCl | 0.5 g |
| NH$_4$Cl | 1 g |
| 1M MgSO$_4$ | 2 ml |
| 1M CaCl$_2$ | 0.1 ml |
| 1% (w/v) thiamine | 1.0 ml |
| 20% (w/v) Brij35 | 20 ml |
| sodium dodecanoate (final 0.5%) | 5 g |

Figure 11:
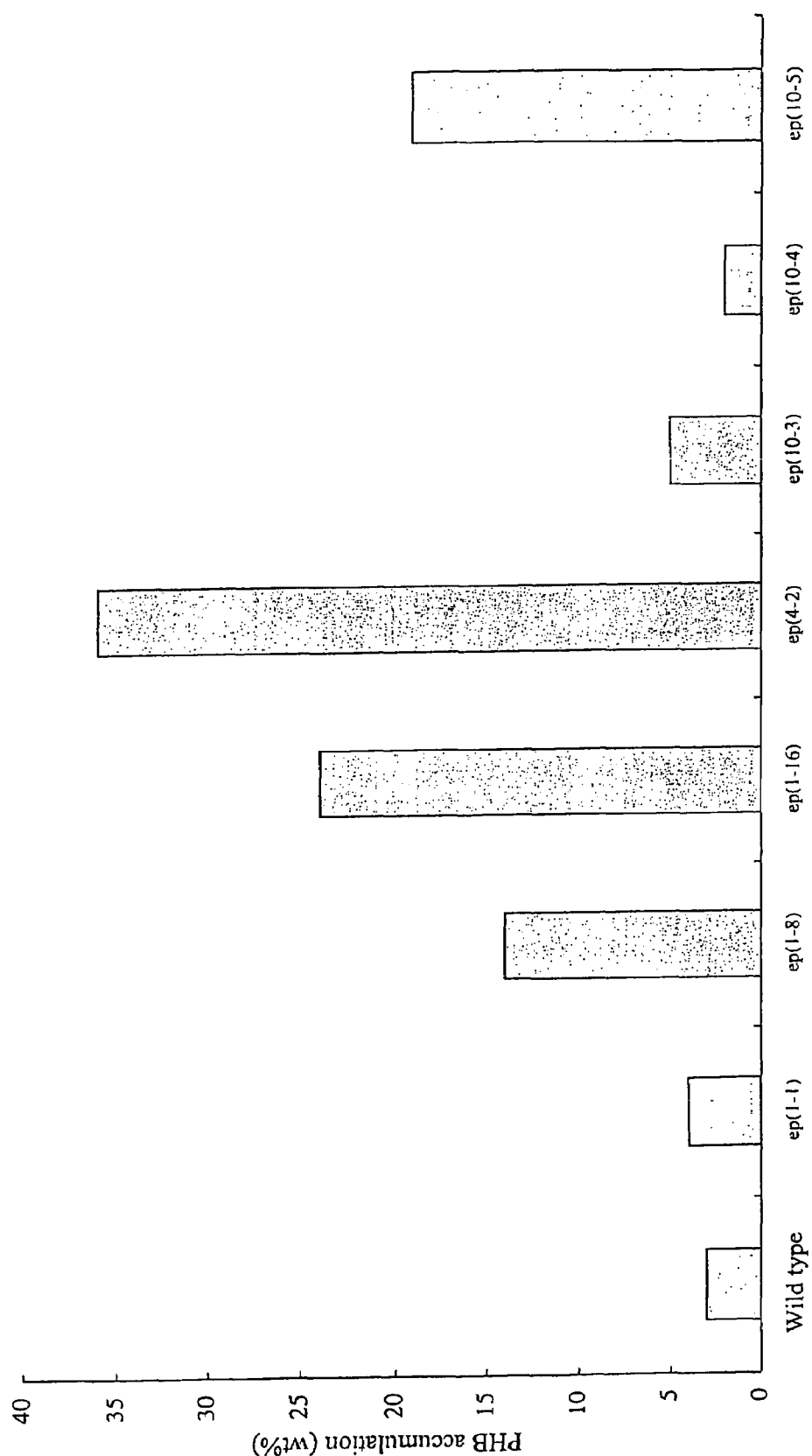
FIG. 11 is a characteristic diagram showing the results of PHA accumulation in mutant PhaCl$_{Ps}$ expression strains and the wild-type PhaCl$_{Ps}$ expression strain.
Figure 12:
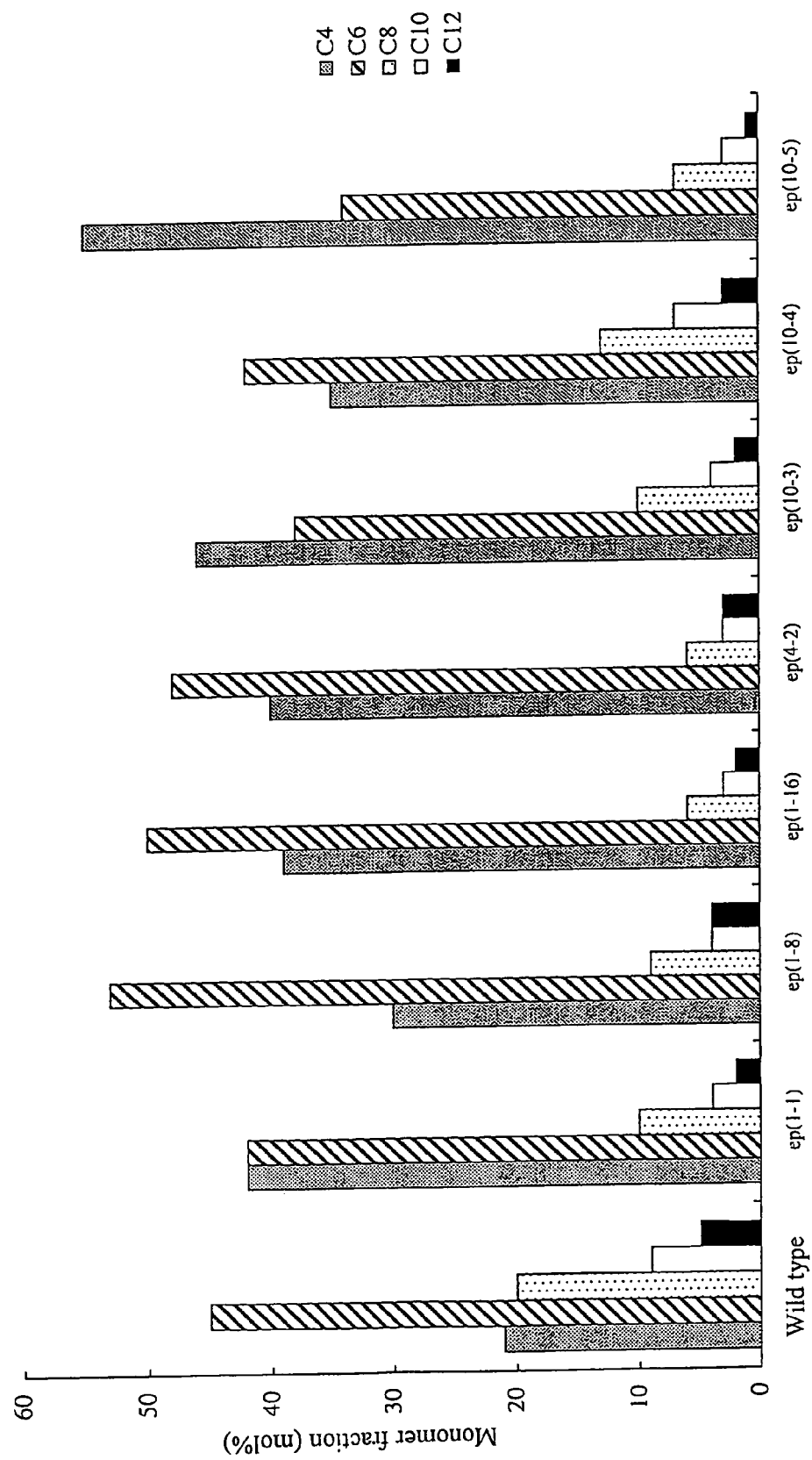
FIG. 12 is a characteristic diagram showing the monomer fractions in mutant PhaCl$_{Ps}$ expression strains and the wild-type PhaCl$_{Ps}$ expression strain.

After incubation, the intracellular P(3HB-co-3HA) copolymer content and the fraction of 3HA monomers constituting P(3HB-co-3HA) were measured. For the measurement of the P(3HB-co-3HA) copolymer content and the fraction of the 3HA monomers, first about 30 mg of dried bacterial body was processed in a solution consisting of 1.7 ml of methanol, 0.3 ml of 98% sulfuric acid and 2.0 ml of chloroform at 100° C. for 140 minutes for methanolysis to convert the P(3HB-co-3HA) copolymer composition into methyl ester. 1 ml of water was added to the reaction mixture for phase separation. Then, the lower chloroform layer was subjected to assay by gas chromatography. For the gas chromatographic assay, Shimadzu GC-17A system was used with a Neutrabond-I capillary column and a flame ionization detector. Results are shown in FIGS. 11 and 12 and Table 8. In Table 7 and FIG. 12, 3HA having 4, 6, 8, 10 and 12 carbon atoms are represented as "C$_4$," "C$_6$," "C$_8$," "C$_{10}$" and "C$_{12}$," respectively.

TABLE 8

| Mutant (amino acid substitution) | PHA content (wt %) | Monomer fraction (mol %) | | | | |
|---|---|---|---|---|---|---|
| | | C4 | C6 | C8 | C10 | C12 |
| Wild strain | 3 | 21 | 45 | 20 | 9 | 5 |
| 1-1 (R27H/S477R) | 4 | 42 | 42 | 10 | 4 | 2 |
| 1-8 (N16T/M292V/S325T) | 14 | 30 | 53 | 9 | 4 | 4 |
| 1-16 (S325C) | 24 | 39 | 50 | 6 | 3 | 2 |
| 4-2 (S325C/H350Y) | 36 | 40 | 48 | 6 | 3 | 3 |
| 10-3 (Q481R) | 5 | 46 | 38 | 10 | 4 | 2 |
| 10-4 (L20P/Q481R) | 2 | 35 | 42 | 13 | 7 | 3 |
| 10-5 (N5D/Q481K) | 19 | 55 | 34 | 7 | 3 | 1 |

As shown in Table 8, the wild-type *E. coli* LS5218 contained 3% by weight P(3HB-co-3HA) copolymers on the dry bacterium weight basis, and the fraction of C$_4$ (3HA having 4 carbon atoms), C$_6$ (ditto), C$_8$ (ditto), C$_{10}$ (ditto) and C$_{12}$ (ditto) was 21%, 45%, 20%, 9% and 5%, respectively. In contrast, the P(3HB-co-3HA) copolymer content in ep(1-8), ep(1-16), ep(4-2) and ep(10-5) was 4.7 times, 8 times, 12 times and 9.5 times that for the wild type, respectively.

In addition, the fraction of the 3HB monomer (C4) in ep(1-8), ep(1-16), ep(4-2) and ep(10-5) was 30%, 39%, 40% and 55%, respectively; copolymers with higher 3HB fractions were produced than those produced by the wild type.

EXAMPLE 4

In Example 4, the P(3HB-co-3HA) copolymer content in PhaCl$_{Ps}$ expression strains having one of the substitutions at positions 130, 477, 325 and 481 and PhaCl$_{Ps}$ expression strains having combinations of these mutations (double mutations, triple mutations and quadruple mutations), and the fractions of 3HA monomers constituting the P(3HB-co-3HA) were examined.

Figure 13:
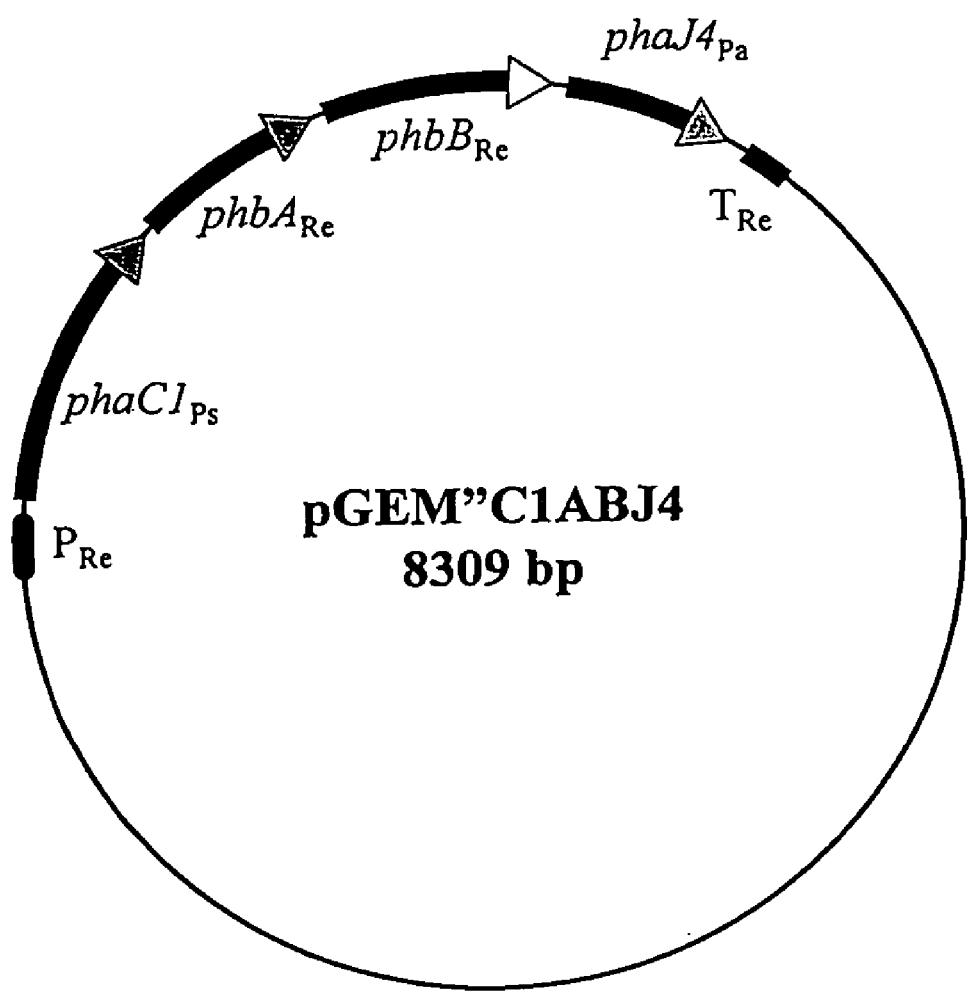
FIG. 13 is a schematic diagram of the plasmid vector pGEM"ClABJ4.

In this example, a plasmid vector pGEM"ClABJ4 was used in which the (R)-specific enoyl CoA hydratase gene (phaJ$_{Ac}$) in the plasmid vector pGEM"Cl$_{Ps}$AB$_{Re}$J$_{Ac}$ used in Example 3, which is derived from *Aeromonas caviae*, was substituted by the (R)-specific enoyl CoA hydratase gene (phaJ4$_{Pa}$) derived from *Pseudomonas aeruginosa* (FIG. 13). The (R)-specific enoyl CoA hydratase gene (phaJ4$_{Pa}$) derived from *Pseudomonas aeruginosa* was obtained by digesting the plasmid vector pUCJ4 described in Tsuge, T. et. al., Int. J. Biol. Micromol. 31. 195 (2003) with restriction enzymes.

Next, the plasmid vector pGEM"ClABJ4 was used to transform *E. coli* LS5218. The transformed *E. coli* LS5218 was incubated as in Example 3 in M9 culture medium containing 0.3% dodecanoic acid and 100 μg/ml ampicillin. After incubation, the intracellular P(3HB-co-3HA) copolymer content and the fraction of 3HA monomers constituting the P(3HB-co-3HA) were measured as in Example 3. Results are shown in Tables 9 and 10.

TABLE 9

|  |  | PHA accumulation (wt %) | Monomer fraction (mol %) | | | | |
|---|---|---|---|---|---|---|---|
|  |  |  | 3HB (C4) | 3HHx (C6) | 3HO (C8) | 3HD (C10) | 3HDD (C12) |
|  | Wild-type enzyme | 13 | 14 | 20 | 38 | 18 | 10 |
| Single mutation | E130D | 20 | 17 | 21 | 35 | 17 | 10 |
|  | S325C | 15 | 20 | 22 | 33 | 16 | 9 |
|  | S325T | 22 | 17 | 22 | 31 | 19 | 11 |
|  | S477R | 6 | 27 | 36 | 25 | 9 | 3 |
|  | Q481K | 13 | 40 | 29 | 20 | 8 | 3 |
|  | Q481M | 20 | 33 | 27 | 24 | 11 | 5 |
|  | Q481R | 7 | 32 | 28 | 26 | 10 | 4 |
| Double mutation | E130D/S325C | 23 | 17 | 23 | 30 | 19 | 11 |
|  | E130D/S325T | 17 | 13 | 25 | 31 | 20 | 11 |
|  | E130D/S477R | — | — | — | — | — | — |
|  | E130D/Q481K | — | — | — | — | — | — |
|  | E130D/Q481M | — | — | — | — | — | — |
|  | E130D/Q481R | — | — | — | — | — | — |
|  | S325C/S477R | — | — | — | — | — | — |
|  | S325T/S477R | — | — | — | — | — | — |
|  | S325C/Q481K | 29 | 36 | 28 | 21 | 10 | 5 |
|  | S325C/Q481M | 34 | 32 | 26 | 24 | 12 | 6 |
|  | S325C/Q481R | 31 | 30 | 27 | 24 | 13 | 6 |
|  | S325T/Q481K | 23 | 27 | 29 | 24 | 13 | 7 |
|  | S325T/Q481M | 22 | 25 | 27 | 25 | 15 | 8 |
|  | S325T/Q481R | 21 | 28 | 27 | 25 | 13 | 7 |
|  | S477R/Q481K | — | — | — | — | — | — |
|  | S477R/Q481M | — | — | — | — | — | — |
|  | S477R/Q481R | — | — | — | — | — | — |

TABLE 10

|  |  | PHA accumulation (wt %) | Monomer fraction (mol %) | | | | |
|---|---|---|---|---|---|---|---|
|  |  |  | 3HD (C4) | 3HHx (C6) | 3HO (C8) | 3HD (C10) | 3HDD (C12) |
| Triple mutation | E130D/S325C/S477R | 24 |  | 32 | 22 | 10 | 5 |
|  | E130D/S325T/S477R | 15 | 22 | 31 | 25 | 14 | 8 |
|  | E130D/S325C/Q481K | 15 | 36 | 28 | 21 | 10 | 5 |
|  | E130D/S325C/Q481M | 13 | 32 | 27 | 23 | 12 | 6 |
|  | E130D/S325C/Q481R | 16 | 37 | 27 | 21 | 10 | 5 |
|  | E130D/S325T/Q481K | 9 | 28 | 31 | 23 | 12 | 6 |
|  | E130D/S325T/Q481M | 11 | 21 | 30 | 26 | 15 | 8 |
|  | E130D/S325T/Q481R | 11 | 23 | 29 | 26 | 14 | 8 |
|  | E130D/S477R/Q481K | 9 | 47 | 27 | 15 | 7 | 4 |
|  | E130D/S477R/Q481M | 12 | 48 | 29 | 14 | 6 | 3 |
|  | E130D/S477R/Q481R | 4 | 53 | 26 | 13 | 5 | 3 |
|  | S325C/S477R/Q481K | 14 | 50 | 27 | 14 | 6 | 3 |
|  | S325C/S477R/Q481M | 10 | 53 | 27 | 13 | 5 | 2 |
|  | S325C/S477R/Q481R | 7 | 55 | 26 | 12 | 5 | 2 |
|  | S325T/S477R/Q481K | 20 | 41 | 28 | 18 | 9 | 4 |
|  | S325T/S477R/Q481M | 13 | 47 | 29 | 15 | 6 | 3 |
|  | S325T/S477R/Q481R | 20 | 45 | 28 | 16 | 7 | 4 |
| Quadruple mutation | E130D/S325C/S477R/Q481K | 11 | 51 | 26 | 14 | 6 | 3 |
|  | E130D/S325C/S477R/Q481M | 7 | 54 | 27 | 12 | 5 | 2 |
|  | E130D/S325C/S477R/Q481R | 12 | 52 | 26 | 13 | 6 | 3 |
|  | E130D/S325T/S477R/Q481K | 11 | 39 | 30 | 18 | 9 | 4 |
|  | E130D/S325T/S477R/Q481M | 3 | 42 | 34 | 16 | 6 | 2 |
|  | E130D/S325T/S477R/Q481R | 11 | 45 | 29 | 16 | 7 | 3 |

Results in Tables 9 and 10 show that the PhaCl$_{Ps}$ expression strain having the E130D single mutation showed an increased P(3HB-co-3HA) accumulation compared to the wild strain, and synthesized P(3HB-co-3HA) having a 3HA monomer fraction similar to the wild strain. The results also showed that the PhaCl$_{Ps}$ expression strain having the S477R single mutation had a different 3HA monomer fraction than the wild strain, and synthesized P(3HB-co-3HA) having a higher fraction of 3HHx containing 6 carbon atoms. The results also showed that the PhaCl$_{Ps}$ expression strain having the S325C, S325T, Q481K, Q481M or Q481R single mutation had a different 3HA monomer fraction than the wild strain, and synthesized P(3HB-co-3HA) having a higher fraction of 3HB containing 4 carbon atoms. The results also showed that the PhaCl$_{Ps}$ expression strain having the S325C, S325T or Q481M single mutation, in particular, had an increased P(3HB-co-3HA) accumulation compared to the wild strain.

Results of the double-, triple- and quadruple-mutation PhaCl$_{Ps}$ expression strains showed that by combining multiple mutations it would be possible to increase the P(3HB-co-3HA) accumulation and synthesize P(3HB-co-3HA) having varying 3HA monomer fractions. The results also showed that the PhaCl$_{Ps}$ expression strains having triple or quadruple mutations including the S477R mutation, in particular, tended to synthesize P(3HB-co-3HA) having high 3HB and 3HHx fractions compared to the wild strain.

This example demonstrated that P(3HB-co-3HA) with practical properties could be synthesized by substituting at least one amino acid selected from the 130-position, 325-position, 477-position and 481-position amino acids of SEQ ID No. 1.

All publications, patents and patent applications cited herein are incorporated herein by reference.

INDUSTRIAL APPLICABILITY

As described in detail herein, the mutant poly(3-hydroxyalkanoic acid) synthase of the present invention can be used to produce biodegradable polyesters having different composition ratios and physical properties from the biodegradable polyester produced by the wild-type enzyme.

Sequence Listing Free Text

SEQ ID Nos. 2 and 3 represent synthetic DNA.

The invention claimed is:

1. A mutant poly(3-hydroxyalkanoic acid) synthase comprising:
a mutant amino acid sequence derived from SEQ ID NO.: 1, wherein at least one amino acid(s) selected from the group consisting of glutamic acid at position 130, serine at position 325, serine at position 477 and glutamine at position 481 is (are) substituted by another amino acid(s) and wherein additional optional substitutions can be made and wherein the total numbers of substitutions is 1 to 4,
wherein said mutant amino acid sequence has the activity to biosynthesize biodegradable polyester.

2. The mutant poly(3-hydroxyalkanoic acid) synthase according to claim 1, wherein glutamine at position 481 is substituted by glycine, lysine, leucine, methionine, arginine, serine or threonine.

3. The mutant poly(3-hydroxyalkanoic acid) synthase according to claim 1, wherein glutamine at position 481 is substituted by lysine, arginine or methionine.

4. The mutant poly(3-hydroxyalkanoic acid) synthase according to claim 1, wherein the amino acid substitution at position 130 is aspartic acid, the amino acid substitution at position 325 is selected from the group consisting of cysteine and threonine, the amino acid substitution at position 477 is arginine, and the amino acid substitution at position 481 is selected from the group consisting of glycine, lysine, leucine, methionine, arginine, serine and threonine.

5. The mutant poly(3-hydroxyalkanoic acid) synthase according to claim 1, which is selected from the group consisting of individual mutant poly(3-hydroxyalkanoic acid) synthase with amino acid substitutions E130D, S325C, S325T, S477R, Q481K, Q481M, Q481R, E130D and S325C, E130D and S325T, E130D and S477R, E130D and Q481K, E130D and Q481M, E130D and Q481R, S325C and S477R, S325T and S477R, S325C and Q481K, S325C and Q481M, S325C and Q481R, S325T and Q481K, S325T and Q481M and S325T and Q481R, E130D and S325C and S477R, E130D and S325T and S477R, E130D and S325C and Q481K, E130D and S325C and Q481M, E130D and S325C and Q481R, E130D and S325T and Q481K, E130D and S325T and Q481M, E130D and S325T and Q481R, E130D and S477R and Q481K, E130D and S477R and Q481M, E130D and S477R and Q481R, S325C and S477R and Q481K, S325C and S477R and Q481M, S325C and S477R and Q481R, S325T and S477R and Q481K, S325T and S477R and Q481M, S325T and S477R and Q481R, E130D and S325C and S477R and Q481K, E130D and S325C and S477R and Q481M, E130D and S325C and S477R and Q481R, E130D and S325T and S477R and Q481K, E130D and S325T and S477R and Q481M, and E130D and S325T and S477R and Q481R.

6. The mutant poly(3-hydroxyalkanoic acid) synthase according to claim 2, wherein the amino acid substitution at position 481 is the only substitution.

7. The mutant poly(3-hydroxyalkanoic acid) synthase according to claim 1, which is selected from the group consisting of a mutant poly(3-hydroxyalkanoic acid) synthase with amino acid substitutions R27H and S477R, S325C and H350Y, L20P and Q481R, N5D and Q481K, and N16T and M292V and S325T.

8. The mutant poly(3-hydroxyalkanoic acid) according to claim 1, wherein the optional substitutions are limited to positions 5, 12, 16, 20, 27, 30, 115, 247, 292, 304, 350, 362, 369, 497 and 547.

9. The mutant poly(3-hydroxyalkanoic acid) according to claim 8 which contains at least one of said optional substitutions.

10. A mutant poly(3-hydroxyalkanoic acid) synthase comprising:
a mutant amino acid sequence derived from SEQ ID NO.: 1, wherein the amino acid glutamine at position 481 is substituted by another amino acid selected from the group consisting of glycine, lysine, leucine, methionine, arginine, serine and threonine, wherein additional optional substitutions can be made and wherein the total numbers of substitutions is 1 to 4, wherein said mutant amino acid sequence has the activity to biosynthesize biodegradable polyester.

11. The mutant poly(3-hydroxyalkanoic acid) synthase according to claim 10, wherein the substitution at amino acid position 481 is glycine.

12. The mutant poly(3-hydroxyalkanoic acid) synthase according to claim 10, wherein the substitution at amino acid position 481 is lysine.

13. The mutant poly(3-hydroxyalkanoic acid) synthase according to claim 10, wherein the substitution at amino acid position 481 is leucine.

14. The mutant poly(3-hydroxyalkanoic acid) synthase according to claim 10, wherein the substitution at amino acid position 481 is methionine.

15. The mutant poly(3-hydroxyalkanoic acid) synthase according to claim 10, wherein the substitution at amino acid position 481 is arginine.

16. The mutant poly(3-hydroxyalkanoic acid) synthase according to claim 10, wherein the substitution at amino acid position 481 is serine.

17. The mutant poly(3-hydroxyalkanoic acid) synthase according to claim 10, wherein the substitution at amino acid position 481 is threonine.

18. The mutant poly(3-hydroxyalkanoic acid) synthase according to any one of claims 11-17, wherein said substitution at position 481 is the only substitution.

* * * * *

SEQUENCE LISTING

```
<160> NUMBER OF SEQ ID NOS: 3

<210> SEQ ID NO 1
<211> LENGTH: 559
<212> TYPE: PRT
<213> ORGANISM: Pseudomonas sp.61-3

<400> SEQUENCE: 1

Met Ser Asn Lys Asn Ser Asp Asp Leu Asn Arg Gln Ala Ser Glu Asn
  1               5                  10                  15

Thr Leu Gly Leu Asn Pro Val Ile Gly Leu Arg Gly Lys Asp Leu Leu
             20                  25                  30

Thr Ser Ala Arg Met Val Leu Thr Gln Ala Ile Lys Gln Pro Ile His
         35                  40                  45

Ser Val Lys His Val Ala His Phe Gly Ile Glu Leu Lys Asn Val Met
     50                  55                  60

Phe Gly Lys Ser Lys Leu Gln Pro Glu Ser Asp Asp Arg Arg Phe Asn
 65                  70                  75                  80

Asp Pro Ala Trp Ser Gln Asn Pro Leu Tyr Lys Arg Tyr Leu Gln Thr
                 85                  90                  95

Tyr Leu Ala Trp Arg Lys Glu Leu His Asp Trp Ile Gly Asn Ser Lys
            100                 105                 110

Leu Ser Glu Gln Asp Ile Asn Arg Ala His Phe Val Ile Thr Leu Met
        115                 120                 125

Thr Glu Ala Met Ala Pro Thr Asn Ser Ala Ala Asn Pro Ala Ala Val
    130                 135                 140

Lys Arg Phe Phe Glu Thr Gly Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
        195                 200                 205

Thr Thr Glu Gln Val His Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Thr Tyr Ile Asp
            260                 265                 270

Ala Leu Lys Glu Ala Val Asp Val Val Ser Ala Ile Thr Gly Ser Lys
        275                 280                 285
```

```
Asp Ile Asn Met Leu Gly Ala Cys Ser Gly Gly Ile Thr Cys Thr Ala
    290                 295                 300
Leu Leu Gly His Tyr Ala Ala Leu Gly Glu Lys Lys Val Asn Ala Leu
305                 310                 315                 320
Thr Leu Leu Val Ser Val Leu Asp Thr Thr Leu Asp Ser Gln Val Ala
                325                 330                 335
Leu Phe Val Asp Glu Lys Thr Leu Glu Ala Ala Lys Arg His Ser Tyr
            340                 345                 350
Gln Ala Gly Val Leu Glu Gly Arg Asp Met Ala Lys Val Phe Ala Trp
        355                 360                 365
Met Arg Pro Asn Asp Leu Ile Trp Asn Tyr Trp Val Asn Asn Tyr Leu
370                 375                 380
Leu Gly Asn Glu Pro Pro Val Phe Asp Ile Leu Phe Trp Asn Asn Asp
385                 390                 395                 400
Thr Thr Arg Leu Pro Ala Ala Phe His Gly Asp Leu Ile Glu Met Phe
                405                 410                 415
Lys Asn Asn Pro Leu Val Arg Ala Asn Ala Leu Glu Val Ser Gly Thr
            420                 425                 430
Pro Ile Asp Leu Lys Gln Val Thr Ala Asp Ile Tyr Ser Leu Ala Gly
        435                 440                 445
Thr Asn Asp His Ile Thr Pro Trp Lys Ser Cys Tyr Lys Ser Ala Gln
450                 455                 460
Leu Phe Gly Gly Lys Val Glu Phe Val Leu Ser Ser Gly His Ile
465                 470                 475                 480
Gln Ser Ile Leu Asn Pro Pro Gly Asn Pro Lys Ser Arg Tyr Met Thr
                485                 490                 495
Ser Thr Asp Met Pro Ala Thr Ala Asn Glu Trp Gln Glu Asn Ser Thr
            500                 505                 510
Lys His Thr Asp Ser Trp Trp Leu His Trp Gln Ala Trp Gln Ala Glu
        515                 520                 525
Arg Ser Gly Lys Leu Lys Lys Ser Pro Thr Ser Leu Gly Asn Lys Ala
530                 535                 540
Tyr Pro Ser Gly Glu Ala Ala Pro Gly Thr Tyr Val His Glu Arg
545                 550                 555

<210> SEQ ID NO 2
<211> LENGTH: 30
<212> TYPE: DNA
<213> ORGANISM: Artificial Sequence
<220> FEATURE:
<223> OTHER INFORMATION: forward primer pETMCS-for

<400> SEQUENCE: 2
cccaacgctg cccgagatct cgatcccgcg                                    30

<210> SEQ ID NO 3
<211> LENGTH: 30
<212> TYPE: DNA
<213> ORGANISM: Artificial Sequence
<220> FEATURE:
<223> OTHER INFORMATION: reverse primer pETMCS-rev

<400> SEQUENCE: 3
agcttccttt cgggctttgt tagcagccgg                                    30
```